(12) United States Patent (10) Patent No.: US 7,927,784 B2
Simpson (45) Date of Patent: Apr. 19, 2011

(54) VASCULAR LUMEN DEBULKING CATHETERS AND METHODS

(75) Inventor: John B. Simpson, Woodside, CA (US)

(73) Assignee: EV3, Plymouth, MN (US)

( * ) Notice: Subject to any disclaimer, the term of this patent is extended or adjusted under 35 U.S.C. 154(b) by 769 days.

(21) Appl. No.: 11/328,453

(22) Filed: Jan. 10, 2006

(65) Prior Publication Data

US 2006/0239982 A1  Oct. 26, 2006

Related U.S. Application Data

(63) Continuation-in-part of application No. 11/108,887, filed on Apr. 19, 2005, which is a continuation-in-part of application No. 10/896,741, filed on Jul. 21, 2004, now Pat. No. 7,699,790, which is a continuation-in-part of application No. 10/288,559, filed on Nov. 4, 2002, now abandoned, which is a continuation-in-part of application No. 10/027,418, filed on Dec. 19, 2001, now Pat. No. 7,771,444.

(60) Provisional application No. 60/381,632, filed on May 19, 2002, provisional application No. 60/272,273, filed on Feb. 27, 2001, provisional application No. 60/257,704, filed on Dec. 20, 2000.

(51) Int. Cl.
*A01N 1/00* (2006.01)
(52) U.S. Cl. ......................................... 435/1.1; 606/129
(58) Field of Classification Search .................. None
See application file for complete search history.

(56) References Cited

U.S. PATENT DOCUMENTS

| | | | |
|---|---|---|---|
| 2,178,790 A | 11/1939 | Henry | |
| 3,705,577 A | 12/1972 | Sierra | |
| 3,815,604 A | 6/1974 | O'Malley et al. | |
| 3,837,345 A | 9/1974 | Matar | |
| 3,995,619 A | 12/1976 | Glatzer | |
| 4,210,146 A | 7/1980 | Banko | |
| 4,669,469 A | 6/1987 | Gifford et al. | |

(Continued)

FOREIGN PATENT DOCUMENTS

EP 0 999 447 A1 5/2000

(Continued)

OTHER PUBLICATIONS

Urayama et al, Surgery Today in Jpn J Surg, 1993, vol. 23, No. 10, pp. 936-938.*

(Continued)

*Primary Examiner* — Allison M Ford
(74) *Attorney, Agent, or Firm* — Mintz, Levin, Cohn, Ferris, Glovsky and Popeo, P.C.

(57) ABSTRACT

A debulking catheter comprising a tissue debulking assembly for removing a continuous strand of material from a body lumen. Catheters of the present invention generally include a catheter body having proximal and distal portions and a tissue debulking assembly disposed at least partially within the distal portion. The tissue debulking assembly is radially movable to expose at least a portion of the assembly through a window on the catheter body. The catheter is advanced transluminally through the body lumen to contact material in the body lumen and remove a plane of continuous material that has a length that is typically longer than a length of the window on the catheter. The continuous material may be directed into a collection chamber. Thereafter, the material may be removed from the collection chamber and preserved or tested.

50 Claims, 27 Drawing Sheets

U.S. PATENT DOCUMENTS

| | | |
|---|---|---|
| 4,696,298 A | 9/1987 | Higgins et al. |
| 4,771,774 A | 9/1988 | Simpson et al. |
| 4,781,186 A | 11/1988 | Simpson et al. |
| 4,817,613 A | 4/1989 | Jaraczewski et al. |
| 4,819,635 A | 4/1989 | Shapiro |
| 4,850,957 A | 7/1989 | Summers |
| 4,926,858 A | 5/1990 | Gifford, III et al. |
| RE33,258 E | 7/1990 | Onik et al. |
| 4,966,604 A | 10/1990 | Reiss |
| 4,979,951 A | 12/1990 | Simpson |
| 4,986,807 A | 1/1991 | Farr |
| 4,994,067 A | 2/1991 | Summers |
| 5,024,651 A | 6/1991 | Shiber |
| 5,047,040 A | 9/1991 | Simpson et al. |
| 5,053,044 A | 10/1991 | Mueller et al. |
| 5,071,425 A | 12/1991 | Gifford et al. |
| 5,084,010 A | 1/1992 | Plaia et al. |
| 5,087,265 A | 2/1992 | Summers |
| 5,092,873 A | 3/1992 | Simpson et al. |
| 5,154,724 A | 10/1992 | Andrews |
| 5,181,920 A | 1/1993 | Mueller et al. |
| 5,217,474 A | 6/1993 | Zacca et al. |
| 5,222,966 A | 6/1993 | Perkins et al. |
| 5,224,488 A | 7/1993 | Neuffer |
| 5,224,949 A | 7/1993 | Gomringer et al. |
| 5,226,909 A | 7/1993 | Evans et al. |
| 5,226,910 A | 7/1993 | Kajiyama et al. |
| 5,242,460 A | 9/1993 | Klein et al. |
| 5,250,059 A | 10/1993 | Andreas et al. |
| 5,250,065 A | 10/1993 | Clement et al. |
| 5,269,793 A | 12/1993 | Simpson et al. |
| 5,282,484 A | 2/1994 | Reger |
| 5,285,795 A | 2/1994 | Ryan et al. |
| 5,312,425 A | 5/1994 | Evans et al. |
| 5,318,032 A | 6/1994 | Lonsbury et al. |
| 5,318,528 A | 6/1994 | Heaven et al. |
| 5,321,501 A | 6/1994 | Swanson et al. |
| 5,336,616 A * | 8/1994 | Livesey et al. ............... 435/395 |
| 5,372,602 A | 12/1994 | Burke |
| 5,395,313 A | 3/1995 | Naves et al. |
| 5,403,334 A | 4/1995 | Evans et al. |
| 5,419,774 A | 5/1995 | Willard et al. |
| 5,429,136 A | 7/1995 | Milo et al. |
| 5,431,673 A | 7/1995 | Summers et al. |
| 5,441,510 A | 8/1995 | Simpson et al. |
| 5,459,570 A | 10/1995 | Swanson et al. |
| 5,470,415 A | 11/1995 | Perkins et al. |
| 5,485,042 A | 1/1996 | Burke et al. |
| 5,491,524 A | 2/1996 | Hellmuth et al. |
| 5,505,210 A | 4/1996 | Clement |
| 5,507,292 A | 4/1996 | Jang et al. |
| 5,507,760 A | 4/1996 | Wynne et al. |
| 5,507,795 A | 4/1996 | Chiang et al. |
| 5,514,115 A | 5/1996 | Frantzen et al. |
| 5,527,325 A | 6/1996 | Conley et al. |
| 5,549,601 A | 8/1996 | McIntyre et al. |
| 5,569,277 A | 10/1996 | Evans et al. |
| 5,571,122 A | 11/1996 | Kelly et al. |
| 5,571,130 A | 11/1996 | Simpson et al. |
| 5,584,842 A | 12/1996 | Fogarty et al. |
| 5,620,447 A | 4/1997 | Smith et al. |
| 5,624,457 A | 4/1997 | Farley et al. |
| 5,632,754 A | 5/1997 | Farley et al. |
| 5,634,464 A | 6/1997 | Jang et al. |
| 5,643,296 A | 7/1997 | Hundertmark et al. |
| 5,643,298 A | 7/1997 | Nordgren et al. |
| 5,665,098 A | 9/1997 | Kelly et al. |
| 5,669,920 A | 9/1997 | Conley et al. |
| 5,674,232 A | 10/1997 | Halliburton |
| 5,695,506 A | 12/1997 | Pike et al. |
| 5,700,687 A | 12/1997 | Finn |
| 5,709,698 A | 1/1998 | Adams et al. |
| 5,733,296 A | 3/1998 | Rogers et al. |
| 5,741,270 A | 4/1998 | Hansen et al. |
| 5,776,114 A | 7/1998 | Frantzen et al. |
| 5,803,078 A * | 9/1998 | Brauner ............... 128/207.14 |
| 5,816,923 A | 10/1998 | Milo et al. |
| 5,836,957 A | 11/1998 | Schulz et al. |
| 5,843,103 A | 12/1998 | Wulfman |
| 5,868,685 A | 2/1999 | Powell et al. |
| 5,868,767 A | 2/1999 | Farley et al. |
| 5,911,734 A | 6/1999 | Tsugita et al. |
| 5,916,210 A | 6/1999 | Winston |
| 5,938,671 A | 8/1999 | Katoh et al. |
| 5,948,184 A | 9/1999 | Frantzen et al. |
| 5,951,482 A | 9/1999 | Winston et al. |
| 5,954,745 A | 9/1999 | Gertler et al. |
| 5,968,064 A | 10/1999 | Selmon et al. |
| 5,989,281 A | 11/1999 | Barbut et al. |
| 6,010,449 A | 1/2000 | Selmon et al. |
| 6,013,072 A | 1/2000 | Winston et al. |
| 6,022,362 A | 2/2000 | Lee et al. |
| 6,027,450 A | 2/2000 | Brown et al. |
| 6,027,514 A | 2/2000 | Stine et al. |
| 6,036,656 A | 3/2000 | Slater |
| 6,036,707 A | 3/2000 | Spaulding |
| 6,048,349 A | 4/2000 | Winston et al. |
| 6,063,093 A | 5/2000 | Winston et al. |
| 6,068,638 A | 5/2000 | Makower |
| 6,081,738 A | 6/2000 | Hinohara et al. |
| 6,106,515 A | 8/2000 | Winston et al. |
| 6,120,515 A | 9/2000 | Rogers et al. |
| 6,120,516 A | 9/2000 | Selmon et al. |
| 6,126,649 A | 10/2000 | VanTassel et al. |
| 6,134,003 A | 10/2000 | Tearney et al. |
| 6,157,852 A | 12/2000 | Selmon et al. |
| 6,159,225 A | 12/2000 | Makower |
| 6,183,432 B1 | 2/2001 | Milo |
| 6,190,353 B1 | 2/2001 | Makower et al. |
| 6,191,862 B1 | 2/2001 | Swanson et al. |
| 6,193,676 B1 | 2/2001 | Winston et al. |
| 6,217,527 B1 | 4/2001 | Selmon et al. |
| 6,217,549 B1 | 4/2001 | Selmon et al. |
| 6,221,049 B1 | 4/2001 | Selmon et al. |
| 6,228,076 B1 | 5/2001 | Winston et al. |
| 6,231,546 B1 | 5/2001 | Milo et al. |
| 6,235,000 B1 | 5/2001 | Milo et al. |
| 6,241,667 B1 | 6/2001 | Vetter et al. |
| 6,241,744 B1 | 6/2001 | Imran et al. |
| 6,258,052 B1 | 7/2001 | Milo |
| 6,266,550 B1 | 7/2001 | Selman et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,302,875 B1 | 10/2001 | Makower et al. |
| 6,330,884 B1 | 12/2001 | Kim |
| 6,355,005 B1 | 3/2002 | Powell et al. |
| 6,375,615 B1 | 4/2002 | Flaherty et al. |
| 6,394,976 B1 | 5/2002 | Winston et al. |
| 6,398,798 B2 | 6/2002 | Selmon et al. |
| 6,419,625 B1 * | 7/2002 | Smith ............................ 600/36 |
| 6,428,552 B1 | 8/2002 | Sparks |
| 6,443,966 B1 | 9/2002 | Shiu |
| 6,445,939 B1 | 9/2002 | Swanson et al. |
| 6,447,525 B2 | 9/2002 | Follmer et al. |
| 6,623,496 B2 | 9/2003 | Snow et al. |
| 6,638,233 B2 | 10/2003 | Corvi et al. |
| 2002/0022788 A1 | 2/2002 | Corvi et al. |
| 2002/0077642 A1 | 6/2002 | Patel et al. |
| 2003/0018346 A1 | 1/2003 | Follmer et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2004/0167553 A1 | 8/2004 | Simpson |
| 2004/0167554 A1 | 8/2004 | Simpson et al. |
| 2005/0154407 A1 | 7/2005 | Simpson et al. |
| 2005/0177068 A1 | 8/2005 | Simpson et al. |
| 2005/0222519 A1 | 10/2005 | Simpson |
| 2005/0222663 A1 | 10/2005 | Simpson et al. |
| 2006/0032508 A1 | 2/2006 | Simpson |
| 2006/0236019 A1 | 10/2006 | Soito et al. |
| 2008/0065124 A1 | 3/2008 | Olson |
| 2008/0065125 A1 | 3/2008 | Olson |

FOREIGN PATENT DOCUMENTS

| | | |
|---|---|---|
| WO | WO 00/18903 | 4/2000 |
| WO | WO 02/19966 A2 | 3/2002 |

| | | | |
|---|---|---|---|
| WO | WO 02/45598 A2 | 6/2002 | |
| WO | WO 03/016910 A1 | 2/2003 | |
| WO | WO 2004/089184 A2 | 10/2004 | |

OTHER PUBLICATIONS

Goes et al, Journal of Clinical Ultrasound (Oct. 1990), vol. 18, pp. 611-617.*
Johnson et al, Journal of the American College of Cardiology (Feb. 1990), vol. 15, No. 2, pp. 419-425.*
Yoffe et al., "Preliminary Experience with the Xtrak Debulking Device in the Treatment of Peripheral Occulasions", Journal of Endovascular Therapy, vol. 9, No. 2, pp. 234-240, (2002).
"MollRing Cutter", Vascular Architects, www.vasculararchitects.com/pages/products_MollRing_Intl.html, Sep. 28, 2004.
Takagi et al., "Effective Plaque Removal With a New 8 French-Compatible Atherectomy Catheter", Catheter Cardiovasc Interv., Aug. 2002, vol. 56, No. 5, pp. 452-459.
"Flexi-Cut® Directional Debulking System: Indications, Contraindications, Warnings, Precautions, Adverse Effects", www.guidant.com/products/ProductTemplates/Vl/dca_ifu.shtml, Sep. 29, 2004.
Rosenthal et al., "Remote Superficial Femoral Artery Endarterectomy and Distal aSpite Stenting: Multicenter Medium-Term Results", Journal of Vascular Surgery, Jul. 2004, vol. 40, No. 1, pp. 67-72.
Ahn et al., "Status of Peripheral Atherectomy", Endovascular Surgery, Surgical Clinics of North America, vol. 72, No. 4, Aug. 1992, pp. 869-878.
Kuffer et al., "Simpson's Atherectomy of the Peripheral Arteries: Early Results and Follow-up", Rofo Fortschr Geb Rontgnestr Neuen Bldgeb Verfahr, Jul. 1990, vol. 153, No. 1, pp. 61-67.
Kuffer, "Peripheral Simpson Atherectomy. Indications and Results of a New Transluminal Procedure for Vascular Recanalization", Radiologe, Feb. 1990, vol. 30, No. 2, pp. 60-65.
Kuffer et al., "Secondary Simpson Atherectomy of Femoro-Popliteal Obstructions. Alternative or Supplementary Procedure to the Femoral Stent?", Vasa Suppl., 1992, vol. 35, p. 187.
Kuffer et al., "Simpson's Atherectomy in Embolizing Leg Artery Stenoses", Rofo Fortschr Geb Rontgenstr Neuen Bildgeb Verfahr, Sep. 1991, vol. 155, No. 3, pp. 235-241.
Steckmeier et al, "Experiences with Rotation Atherectomy and Atherectomy", Herz, Feb. 1989, vol. 14, No. 1, pp. 43-51.
Di Sciascio et al., "Directional Coronary Atherectomy: From Therapeutic Device to Research Tool in Coronary Artery Disease", Cardiologia, Apr. 1999, vol. 44, No. 4, pp. 333-339.
Ikeno et al., "Early Experience With a Novel Plaque Excision System for the Treatment of Complex Coronary Lesions", Catheterization and Cardiovascular Interventions, 2004, vol. 61, pp. 35-43.
Cook et al., "DNA Microarrays: Implications for Cadriovascular Medicine", Circulation Research, 2002, vol. 91, pp. 559-564.
Patino et al., "Serial Analysis of Gene Expression: Technical Considerations and Applications to Cardiovascular Biology", Circulation Research, 2002, vol. 91, pp. 565-569.
Levy et al., "Microarray Analysis of Neointima: Flowing Toward a Clear Future", Arterioscler Thromb Vasc Biol., 2002, vol. 22, pp. 1946-1947.
Ye et al., 'Microarray, SAGE and their Applications to Cardiovascular Diseases', Cell Research, 2002, vol. 12, No. 2, pp. 105-115.
Gonschior et al., "Results of Directional Peripheral Atherectomy with Reference to Histology, Histochemistry, and Ultrastructure", The Journal of Vascular Diseases, Jun. 1993, pp. 454-463.
Johnson et al., "Primary Peripheral Arterial Stenoses and Restenoses Excised by Transluminal Atherectomy: A Histopathologic Study", J Am Coll Cardiol, Feb. 1990, vol. 15, No. 2, pp. 419-425.
Waller et al., "Histologic Analysis of Directional Coronary Atherectomy Samples: A Review of Findings and their Clinical Relevance", The American Journal of Cardiology, Oct. 18, 1993, vol. 72, pp. 80E-87E.
DiSciascio et al., "Histopathologic Correlates of Unstable Ischemic Syndromes in Patients Undergoing Directional Coronary Atherectomy: In Vivo Evidence of Thrombosis, Ulceration, and Inflammation", Am Heart J., Sep. 1994, vol. 128, No. 3, pp. 419-426.
Krings et al., "Ultrastructural and Proliferation Studies of Human, Catheter Atherectomy Extracted Plaque Material", Vasa Suppl., 1991, vol. 33, pp. 149-150.
Bauriedel et al., "Cellularity and Ultrastructural Characteristics of Human Atherectomy Specimens: Comparison Between Resenosis and Primary Stenotic of Coronary and Peripheral Lesions", Z Kardiol., Aug. 1993, vol. 82, No. 8, pp. 485-493.
Hofling et al., "Analysis of Atherectomy Specimens", Am J Cardiol, Oct. 18, 1993, vol. 72, No. 13, pp. 96E-107E.
MacLeod et al., "Proliferation and Extracellular Matrix Synthesis of Smooth Muscles Cultured From Human Coronary Atherosclerotic and Restenotic Lesions", J Am Coll Cardiol., Jan. 1994, vol. 23, No. 1, pp. 59-65.
Hanke et al, "Accumulation of Macrophages in the Arterial Vessel Wall Following Experimental Balloon Angioplasty", Eur Heart J, May 1994, vol. 15, No. 5, pp. 691-698.
Zohlnhöfer et al., "Gene Expression Profiling of Human Stent-Induced Neointima by cDNA Array Analysis of Microscopic Specimens Retrieved by Helix Cutter Atherectomy", Circulation, 2001, vol. 103, pp. 1396-1402.
Williams et al., "Directional Coronary Atherectomy: But Wait, There's More", Circulation, 1998, vol. 97, pp. 309-311.
Hofling et al., "Angiography and Functional Results and Histologic Findings Following Percutaneous Atherectomy in Patients with Arterial Occlusive Disease", Z Kardiol, Sep. 1989, vol. 78, No. 9, pp. 561-566.
Grant et al., "Expression of IGF-I, IGF-I Receptor and IGF Binding Proteins-1, -2, -3, -4 and -5 in Human Atherectomy Specimens", Regul Pept., Dec. 17, 1996, vol. 67, No. 3, pp. 137-144.
Taylor et al., "Proliferative Activity in Coronary Atherectomy Tissue. Clinical, Histopathologic, and Immunohistochemical Correlates", Chest, Sep. 1995, vol. 108, No. 3, pp. 815-820.
Yutani et al., "Histologic Evidence of Foreign Body Granulation Tissue and De Novo Lesions in Patients with Coronary Stent Restenosis", Cardiology, 1999, vol. 92, No. 3, pp. 171-177.
Veinot et al., "Preliminary Clinical Experience with the Pullback Atherectomy Catheter and the Study of Proliferation in Coronary Plaques", Can J Cardiol, Dec. 1998, vol. 14, No. 12, pp. 1457-1463.
Arbustini et al., "Histopathologic Features in Atherectomy Samples Obtained From Patient with Unstable Angina, Stable Angina and Restenosis. Direct Atherectomy Lombardi Group", G Ital Cardiol., Jun. 1996, vol. 26, No. 6, pp. 623-633.
Ellis et al., "Relation of Clinical Presentation, Stenosis Morphology, and Operation Technique to the Procedural Results of Rotational Atherectomy and Rotational Atherectomy-Facilitated Angioplasty", Circulation, Feb. 1994, vol. 89, No. 2, pp. 882-892.
Ellis et al., "Relation of Stenosis Morphology and Clinical Presentation to the Procedural Results of Directional Coronary Atherectomy", Circulation, Aug. 1991, vol. 84, No. 2, pp. 644-653.
Dartsch et al., "Cell Constitution and Characteristics of Human Atherosclerotic Plaque Selectively Removed by Percutaneous Atherectomy", Atherosclerosis, Dec. 1989, vol. 80, No. 2, pp. 149-157.
U.S. Appl. No. 11/010,833, filed Dec. 13, 2004, Simpson.
Ballantyne, et al., "Markers of Inflammation and Their Clinical Significance", Athero Supp. 6:21-29, (2005).
Ballantyne, et al., "Lipoprotein-Associated Phospholipase $A_2$, High-Sensitivity C-Reactive Protein, and Risk for Incident Coronary Heart Disease in Middle-Aged Men and Women in the Atherosclerosis Risk in Communities (ARIC) Study", Circulation 109:837-842 (2004).
Brilakis, et al., "Association of lipoprotein-associated phospholipase A2 levels with coronary artery disease risk factors, angiographic coronary artery disease, and major adverse events at follow-up", European Heart Journal 26(2):137-144 (2005).
Cipollone, et al., "High preprocedural non-HDL cholesterol is associated with enhanced oxidative stress and monocyte activation after coronary angioplasty: possible implications in restenosis" Heart 89:773-779 (2005).
Hojo, et al., "Matrix metalloproteinase expression in the coronary circulation induced by coronary angioplasty" Atherosclerosis. 161:185-193 (2002).

Hojo, et al., "Chemokine expression in coronary circulation after coronary angioplasty as a prognostic factor for restenosis" *Atherosclerosis*. 156:165-170 (2001).

Hojo, et al., "Interleukin 6 expression in coronary circulation after coronary angioplasty as a risk factor for Restenosis" *Heart* 84:83-87 (2000).

Horie, et al., "Association of an Acute Reduction in Lipoprotein(a) With Coronary Artery Restenosis After Percutaneous Transluminal Coronary Angioplasty" *Circulation* 96(1):166-173 (1997).

Inoue, et al., "Expression of Polymorphonuclear Leukocyte Adhesion Molecules and Its Clinical Significance in Patients Treated with Percutaneous Transluminal Coronary Angioplasty" *JACC* 28(5):1127-1133(1996).

Kurz, et al., "Increased serum concentrations of adhesion molecules after coronary angioplasty" *Clinical Science*, 87:627-633 (1994).

Mukherjee, et al., "Elective coronary revascularization, an iatrogenic form of acute coronary syndrome: How can clinicians reduce the risk?", *American Heart Journal* 148(3):371-377 (2004).

Tashiro, et al., "Role of cytokines in the pathogenesis of restenosis after percutaneous transluminal coronary angioplasty" *Coronary Artery Disease* 12(2):107-113 (2001).

Winkler, et al., "Platelet-Activating Factor Acetylhydrolase Activity Indicates Angiographic Coronary Artery Disease Independently of Systemic Inflammation and Other Risk Factors" *Circulation* 111:980-987 (2005).

\* cited by examiner

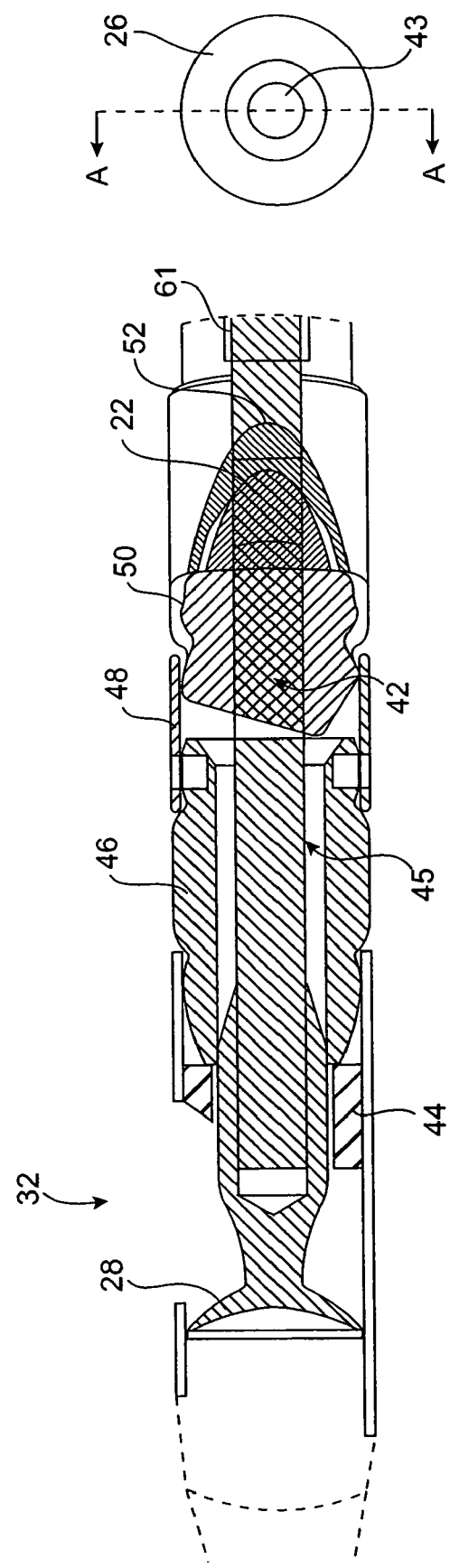

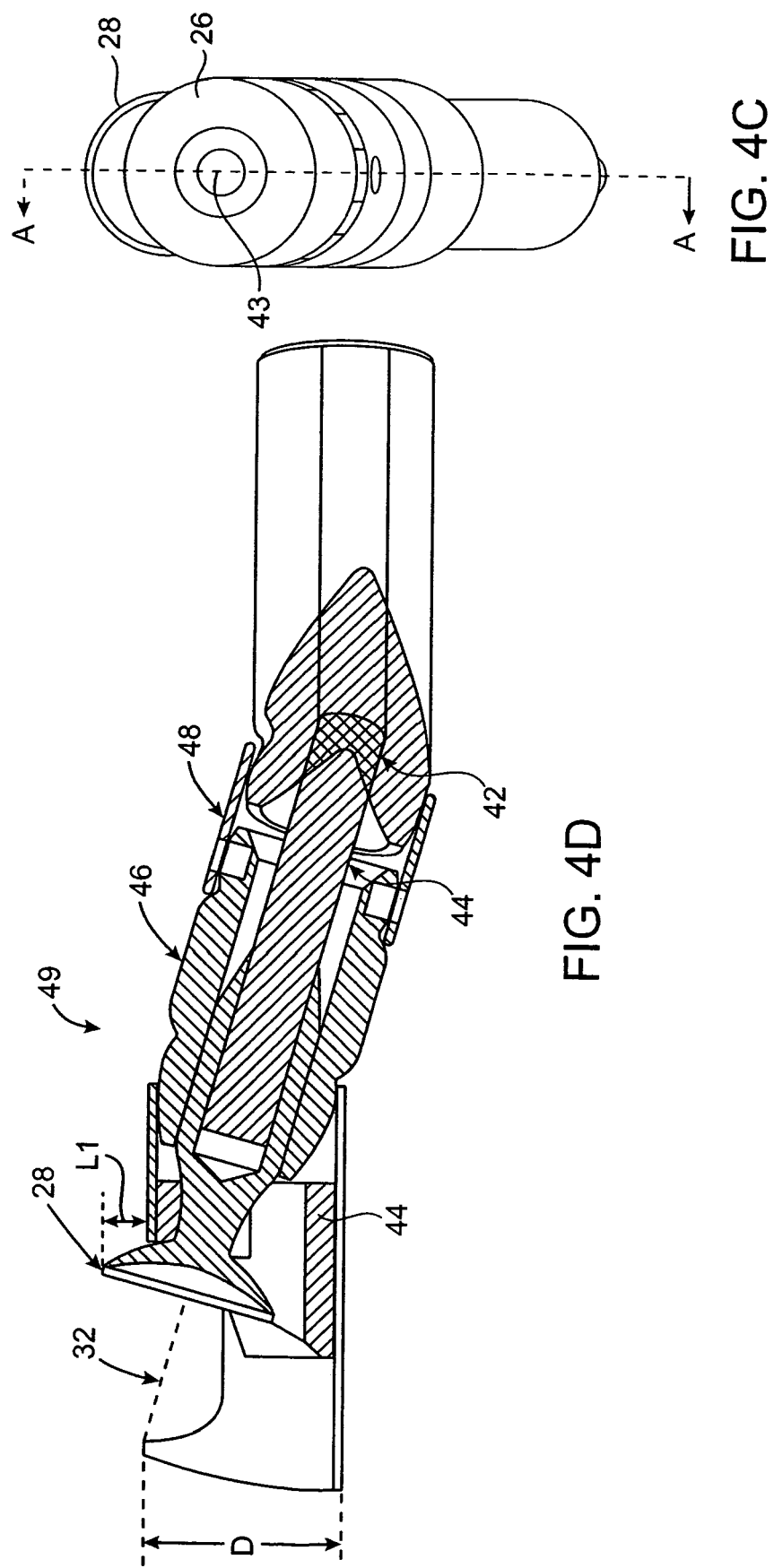

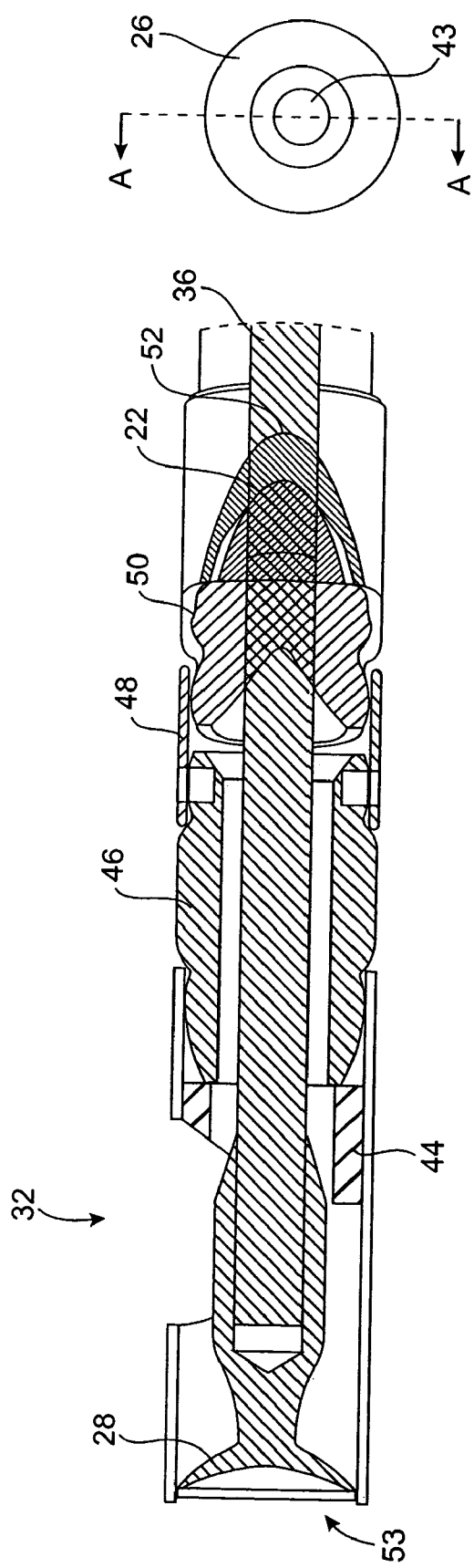

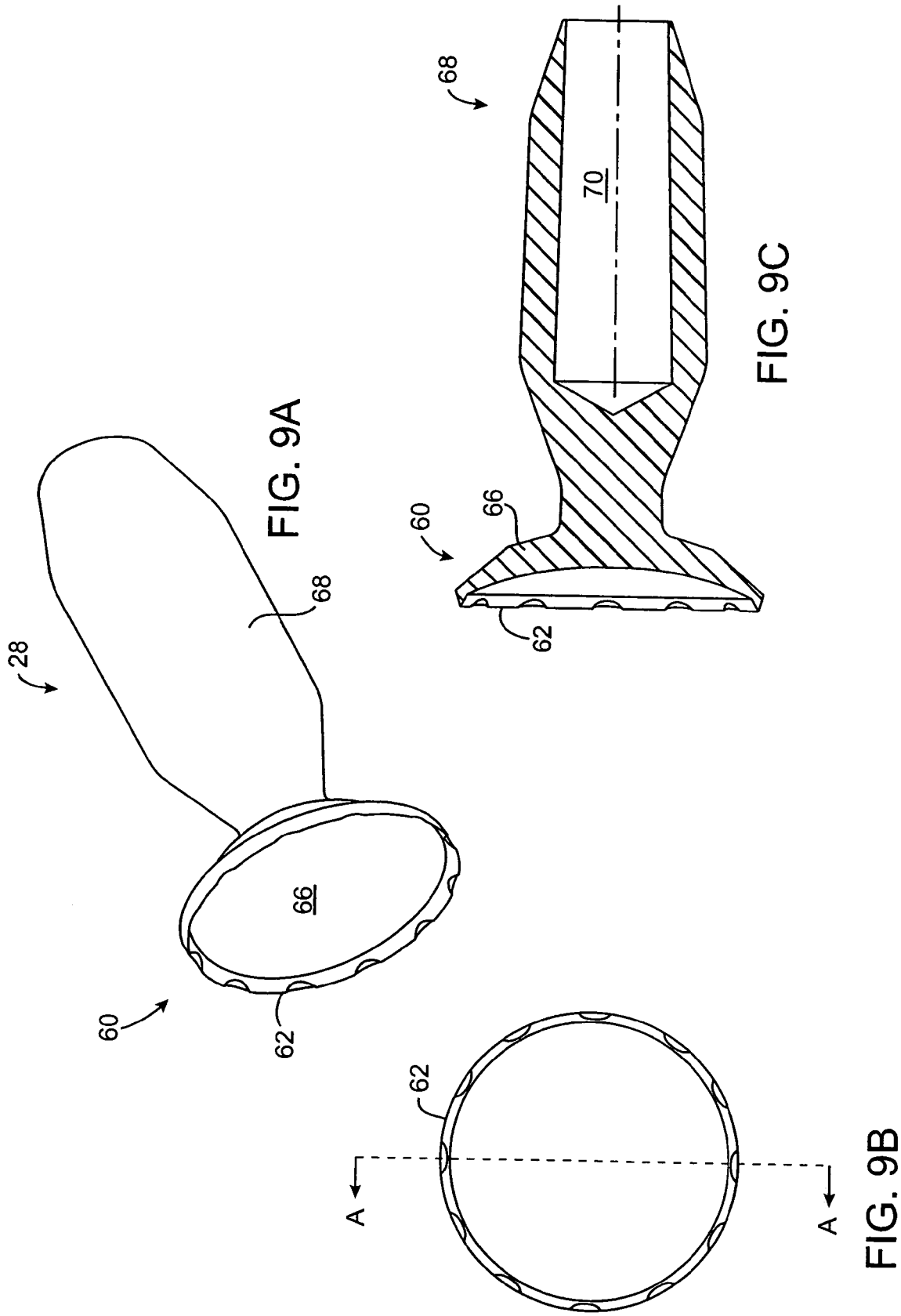

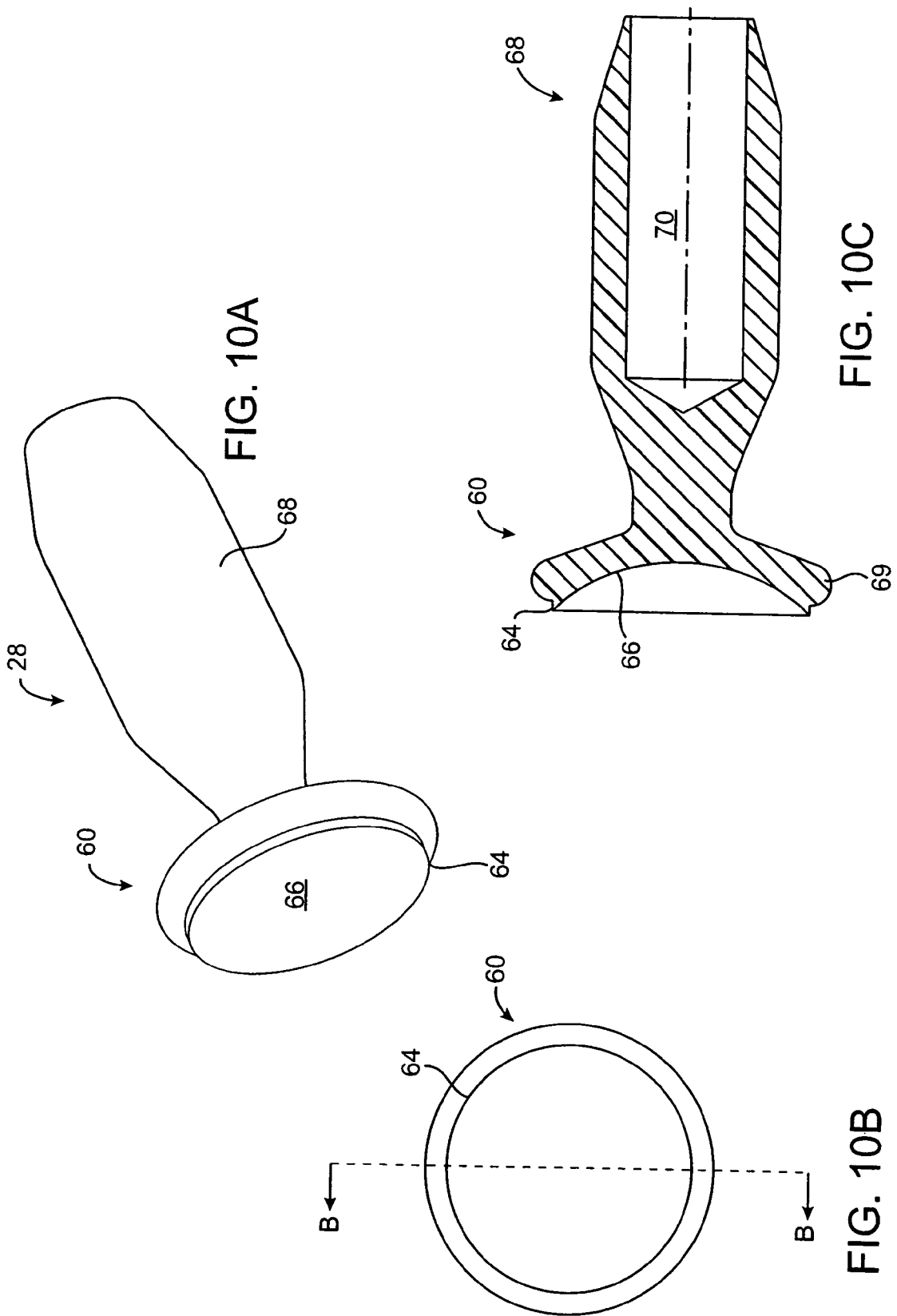

Tissue fragment weight relative to tissue fragment length

| Fragment | Weight of Tissue fragment (mg) | Length of Tissue fragment (mm) | Weight/Length (mg/mm) |
|---|---|---|---|
| 1 | 34.5 | 35 | 0.99 |
| 2 | 14.6 | 20 | 0.73 |
| 3 | 22.5 | 30 | 0.75 |
| 4 | 11.1 | 17 | 0.65 |
| 5 | 3.4 | 7 | 0.49 |
| 6 | 10.7 | 9 | 1.19 |
| 7 | 7.6 | 13 | 0.58 |
| 8 | 6.8 | 12 | 0.57 |
| 9 | 6.2 | 6 | 1.03 |
| 10 | 15.4 | 24 | 0.64 |
| 11 | 20.5 | 27 | 0.76 |
| 12 | 6.3 | 14 | 0.45 |
| 13 | 17.9 | 26 | 0.69 |
| 14 | 15.5 | 21 | 0.74 |
| 15 | 6.2 | 11 | 0.56 |
| 16 | 11.3 | 15 | 0.75 |
| 17 | 22.2 | 31 | 0.72 |
| 18 | 18.3 | 19 | 0.96 |
| 19 | 4.8 | 9 | 0.53 |
| 20 | 3.8 | 8 | 0.48 |
|  |  |  |  |
| Average | 12.98 | 17.7 | 0.73 |
|  | 0.73mg per mm length |  |  |

Markers upregulated in vascular disease

| | |
|---|---|
| AA775616 | osteopontin |
| AA682386 | oxidised low density lipoprotein (lectin-like) receptor 1 |
| AA969504 | interferon, gamma |
| AA102526 | interleukin 8 |
| BU631490 | tissue inhibitor of metalloproteinase 2 |
| NM_002356 | myristoylated alanine-rich protein kinase C substrate |
| NM_000930 | plasminogen activator, tissue |
| NM_002117 | major histocompatibility complex, class I, C |
| AI129421 | interleukin 18 (interferon-gamma-inducing factor) |
| W51794 | matrix metalloproteinase 3 (stromelysin 1, progelatinase) |
| AA143201 | matrix metalloproteinase 1 (interstitial collagenase) |
| N94616 | laminin, alpha 4 |
| NM_021999 | integral membrane protein 2B |
| NM_000584 | interleukin 8 |
| NM_002510 | glycoprotein (transmembrane) nmb |
| N53447 | integral membrane protein 2A |
| NM_002659 | plasminogen activator, urokinase receptor |
| AL133111 | SH3-domain binding protein 5 (BTK-associated) |
| NM_147780 | cathepsin B |
| W46577 | endothelial cell-specific molecule 1 |
| AA857496 | matrix metalloproteinase 10 (stromelysin 2) |
| NM_005502 | ATP-binding cassette, sub-family A (ABC1), member 1 |
| AI342012 | macrophage scavenger receptor 1 |
| AA490846 | integrin, alpha 4 (antigen CD49D, alpha 4 subunit of VLA-4 receptor) |
| AA454999 | hypothetical protein FLJ10111 |
| AK093984 | hypothetical protein MGC5618 |
| AA666269 | integrin, beta 3 (platelet glycoprotein IIIa, antigen CD61) |
| NM_005625 | syndecan binding protein (syntenin) |
| BC014989 | phospholipid scramblase 3 |
| AI279830 | protein phosphatase 1, regulatory (inhibitor) subunit 16B |
| AA936768 | interleukin 1, alpha |
| NM_001920 | decorin |
| AK055130 | calmodulin 2 (phosphorylase kinase, delta) |
| NM_016497 | mitochondrial ribosomal protein L51 |
| AA451863 | CD4 antigen (p55) |
| NM_058197 | cyclin-dependent kinase inhibitor 2A |
| R10284 | hyaluronan-mediated motility receptor (RHAMM) |
| AI309439 | integrin, alpha M (complement component receptor 3, alpha) |
| AI334914 | integrin, alpha 2b |
| AF001893 | multiple endocrine neoplasia I |
| N36136 | endomucin-2 |
| AW772163 | hypothetical protein FLJ20401 |
| NM_001964 | early growth response 1 |
| AA454668 | prostaglandin-endoperoxide synthase 1 |
| NM_004530 | matrix metalloproteinase 2 |
| AK027663 | stanniocalcin 2 |

Fig. 24

AA057204   interleukin 2 receptor, beta
NM_001444  fatty acid binding protein 5 (psoriasis-associated)
AA873792   small inducible cytokine A5 (RANTES)

Markers upregulated in diabetes

AA936768   interleukin 1, alpha
NM_000600  interleukin 6 (interferon, beta 2)
N98591     interleukin 6 (interferon, beta 2)
AA156031   metallothionein 2A
NM_001235  serine (or cysteine) proteinase inhibitor, clade H
BF131637   metallothionein 2A
NM_006216  serine (or cysteine) proteinase inhibitor, clade E
NM_001552  insulin-like growth factor binding protein 4
NM_004530  matrix metalloproteinase 2
NM_000088  collagen, type I, alpha 1
NM_023009  MARCKS-like protein
NM_003670  basic helix-loop-helix domain containing, class B, 2
T80495     Hs. clone 24707 mRNA sequence
NM_002993  chemokine C-X-C motif, granulocyte chemotactic protein 2
NM_006756  transcription elongation factor A (SII), 1
AI983239   Hs. cDNA FLJ32163 fis, clone PLACE6000371
NM_005110  glutamine-fructose-6-phosphate transaminase 2
NM_000584  interleukin 8
AK092836   Homo sapiens cDNA FLJ35517 fis, clone SPLEN2000698
NM_000104  cytochrome P450, subfamily I (dioxin-inducible), peptide
NM_004966  heterogeneous nuclear ribonucleoprotein F
AK025599   mannosidase, alpha, class 1A, member 1
NM_002923  regulator of G-protein signalling 2, 24kDa
AW005755   macrophage migration inhibitory factor
~~AA873792~~   ~~small inducible cytokine A5 (RANTES)~~
U72621     pleiomorphic adenoma gene-like 1
NM_000358  transforming growth factor, beta-induced, 68kDa
AK054688   Homo sapiens cDNA FLJ30126 fis, clone BRACE1000114
BC007583   Homo sapiens, clone MGC:15572 IMAGE:3140342
NM_000089  collagen, type I, alpha 2
NM_004404  neural precursor cell expressed, developmental regulated 5
NM_078467  cyclin-dependent kinase inhibitor 1A (p21, Cip1)
U97105     Homo sapiens N2A3 mRNA, complete cds
AI356451   CD19 antigen
BF732465   tissue inhibitor of metalloproteinase 2
NM_001554  cysteine-rich, angiogenic inducer, 61
BQ890604   Homo sapiens URB mRNA, complete cds
NM_002631  phosphogluconate dehydrogenase
N94503     pregnancy-associated plasma protein A
NM_001710  B-factor, properdin Markers upregulated in normal (non-diabetic) vessel segments

Fig. 24

| | |
|---|---|
| NM_000584 | interleukin 8 |
| N98591 | interleukin 6 (interferon, beta 2) |
| AA936768 | interleukin 1, alpha |
| BM803108 | ESTs |
| NM_000600 | interleukin 6 (interferon, beta 2) |
| AI359876 | EST |
| AA156031 | metallothionein 2A |
| BF131637 | metallothionein 2A |
| NM_003670 | basic helix-loop-helix domain, class B, 2 |
| NM_001235 | serine (or cysteine) proteinase inhibitor, clade H |
| NM_004530 | matrix metalloproteinase 2 |
| NM_002982 | monocyte chemotactic protein 1 |
| NM_002631 | phosphogluconate dehydrogenase |
| NM_078467 | cyclin-dependent kinase inhibitor 1A (p21, Cip1) |
| NM_152862 | actin related protein 2/3 complex, subunit 2 |
| NM_002923 | regulator of G-protein signalling 2, 24kDa |
| AI983239 | Hs. cDNA FLJ32163 fis, clone PLACE6000371 |
| NM_005415 | solute carrier family 20, member 1 |
| AW772163 | hypothetical protein FLJ20401 |
| R21535 | Hs. cDNA FLJ11724 fis, clone HEMBA1005331 |
| NM_005110 | glutamine-fructose-6-phosphate transaminase 2 |
| AK092836 | cDNA FLJ35517 fis, clone SPLEN2000698 |
| NM_006216 | serine (or cysteine) proteinase inhibitor, clade E |

Markers which are downregulated with statin treatment

| | |
|---|---|
| NM000600 | interleukin 6 (interferon, beta 2) |
| N98591 | interleukin 6 (interferon, beta 2) |
| NM_005746 | pre-B-cell colony-enhancing factor |
| NM_002852 | pentaxin-related gene, rapidly induced by IL-1 beta |
| N92901 | fatty acid binding protein 4, adipocyte |
| NM_005110 | glutamine-fructose-6-phosphate transaminase 2 |
| AK094728 | cDNA FLJ37409 fis, similar to COMPLEMENT C3 |
| NM_004000 | chitinase 3-like 2 |
| NM_002923 | regulator of G-protein signalling 2, 24kDa |
| T80495 | Hs. clone 24707 mRNA sequence |
| AA936768 | interleukin 1, alpha |
| NM_145791 | microsomal glutathione S-transferase 1 |
| NM_006169 | nicotinamide N-methyltransferase |
| AW007736 | UDP-glucose ceramide glucosyltransferase |
| NM_005420 | sulfotransferase, estrogen-preferring |
| NM_003670 | basic helix-loop-helix domain containing, class B, 2 |
| AA425102 | monocyte chemotactic protein 1 |
| NM_003254 | tissue inhibitor of metalloproteinase 1 |
| BF131637 | metallothionein 2A |
| NM_000104 | cytochrome P450, subfamily I (dioxin-inducible) |
| NM_001733 | complement component 1, r subcomponent |
| NM_032849 | hypothetical protein FLJ14834 |
| NM_005328 | hyaluronan synthase 2 |
| NM_002009 | fibroblast growth factor 7 (keratinocyte growth factor) |

Fig. 24

| | |
|---|---|
| NM_002615 | serine (or cysteine) proteinase inhibitor, clade F |
| NM_002658 | plasminogen activator, urokinase |
| NM_033439 | DVS27-related protein |
| AA381343 | interleukin 6 (interferon, beta 2) |
| AW780123 | ribosomal protein S26 |
| M14219 | chondroitin/dermatan sulfate proteoglycan (PG40) core |
| AF495759 | Homo sapiens unknown mRNA |
| NM_001679 | ATPase, Na+/K+ transporting, beta 3 polypeptide |
| NM_001029 | ribosomal protein S26 |
| NM_002074 | guanine nucleotide binding protein, beta polypeptide 1 |
| NM_001552 | insulin-like growth factor binding protein 4 |
| AF208043 | interferon, gamma-inducible protein 16 |
| AI268937 | monocyte chemotactic protein 2 |
| AA040170 | monocyte chemotactic protein 3 |
| AW131311 | EST |
| NM_005415 | solute carrier family 20 (phosphate transporter), member 1 |
| NM_006988 | a disintegrin-like and metalloprotease (reprolysin type) |
| NM_006307 | sushi-repeat-containing protein, X chromosome |
| NM_000584 | interleukin 8 |
| D31887 | KIAA0062 protein |
| NM_002229 | jun B proto-oncogene |
| NM_002982 | monocyte chemotactic protein 1 |

Markers downregulated with statin treatment

| | |
|---|---|
| NM_002615 | serine (or cysteine) proteinase inhibitor, clade F |
| AK094728 | Homo sapiens cDNA FLJ37409 fis, clone BRAMY2028516 |
| NM_001552 | insulin-like growth factor binding protein 4 |
| N92901 | fatty acid binding protein 4, adipocyte |
| N98591 | interleukin 6 (interferon, beta 2) |
| NM_000104 | cytochrome P450, subfamily I (dioxin-inducible) |
| NM_006756 | transcription elongation factor A (SII), 1 |
| NM_000600 | interleukin 6 (interferon, beta 2) |
| AF506819 | Homo sapiens URB mRNA, complete cds |
| NM_145791 | microsomal glutathione S-transferase 1 |
| N39161 | CD36 antigen (thrombospondin receptor) |
| M14219 | Human chondroitin sulfate proteoglycan core protein |
| NM_031476 | hypothetical protein DKFZp434B044 |
| NM_000186 | H factor 1 (complement) |
| NM_003254 | tissue inhibitor of metalloproteinase 1 |
| N98591 | interleukin 6 (interferon, beta 2) |
| AJ318805 | ESTs, Weakly similar to hypothetical protein FLJ20378 |
| AA284954 | colony stimulating factor 1 receptor |
| NM_002923 | regulator of G-protein signalling 2, 24kDa |
| NM_001920 | decorin |
| BI830199 | likely ortholog of mouse Urb |
| AA451863 | CD4 antigen (p55) |
| AA464526 | interleukin 1 receptor, type I |
| AW192258 | sprouty homolog 4 (Drosophila) |
| N68859 | intercellular adhesion molecule 1 (CD54) |

Fig. 24

| | |
|---|---|
| BC007552 | Homo sapiens, clone MGC:15473 IMAGE:2967168, mRNA |
| NM_001733 | complement component 1, r subcomponent |
| NM_006288 | Thy-1 cell surface antigen |
| NM_000201 | intercellular adhesion molecule 1 (CD54) |
| R22412 | platelet/endothelial cell adhesion molecule (CD31 antigen) |
| NM_013417 | isoleucine-tRNA synthetase |
| NM_004000 | chitinase 3-like 2 |
| R70506 | growth factor receptor-bound protein 2 |
| NM_030781 | collectin sub-family member 12 |
| NM_001710 | B-factor, properdin |
| NM_006216 | serine (or cysteine) proteinase inhibitor, clade E |
| NM_005110 | glutamine-fructose-6-phosphate transaminase 2 |
| AF506819 | Homo sapiens URB mRNA, complete cds |
| NM_002074 | guanine nucleotide binding protein, beta polypeptide 1 |
| H26022 | fractalkine, inducible cytokine subfamily D (Cys-X3-Cys) |
| AK092836 | Homo sapiens cDNA FLJ35517 fis, clone SPLEN2000698 |
| BQ890604 | Homo sapiens URB mRNA, complete cds |
| AA057204 | interleukin 2 receptor, beta |
| AI524093 | myosin, heavy polypeptide 11, smooth muscle |
| AI655374 | stromal cell-derived factor 1 |

VASCULAR LUMEN DEBULKING CATHETERS AND METHODS

CROSS-REFERENCES TO RELATED APPLICATIONS

The present application is a continuation-in-part of U.S. patent application Ser. No. 11/108,887 filed Apr. 19, 2005, which is a continuation in part of U.S. patent application Ser. No. 10/896,741, filed Jul. 21, 2004, which is a continuation-in-part of U.S. patent application Ser. No. 10/288,559, filed Nov. 4, 2002, which is a continuation-in-part of U.S. patent application Ser. No. 10/027,418, filed Dec. 19, 2001, which claims the benefit of Provisional Patent Application Ser. No. 60/257,704, filed Dec. 20, 2000, and Provisional Patent Application Ser. No. 60/272,273 filed Feb. 27, 2001, the complete disclosures of which are incorporated herein by reference.

Application Ser. No. 10/896,741 also claims the benefit of Provisional Application No. 60/381,632, filed on May 19, 2002, the complete disclosure of which is incorporated herein by reference. The present application is also related to U.S. patent application Ser. No. 09/377,884, filed Aug. 19, 1999, and Ser. No. 09/377,894, filed Aug. 19, 1999, entitled the complete disclosures of which are incorporated by reference.

BACKGROUND OF THE INVENTION

The present invention relates generally to percutaneous transluminal systems and methods for debulking body lumens. More particularly, the present invention relates to atherectomy catheters for excising atheroma and other materials from blood vessels and from stents. The present invention also relates to methods for the selective excision and testing of material from a body lumen, such as a blood vessel.

Cardiovascular disease frequently arises from the accumulation of atheromatous material on the inner walls of vascular lumens, particularly arterial lumens of the coronary and other vasculature, resulting in a condition known as atherosclerosis. Atherosclerosis occurs naturally as a result of aging, but may also be aggravated by factors such as diet, hypertension, heredity, vascular injury, and the like. Atheromatous and other vascular deposits restrict blood flow and can cause ischemia which, in acute cases, can result in myocardial infarction. Atheromatous deposits can have widely varying properties, with some deposits being relatively soft and others being fibrous and/or calcified. In the latter case, the deposits are frequently referred to as plaque.

One conventional treatment for cardiovascular disease is the use of stents. Endoluminal stents are commonly used to treat obstructed or weakened body lumens, such as blood vessels and other vascular lumens. Once deployed in the blood vessel, the stent can remain in the body lumen where it will maintain the patency of the lumen and/or support the walls of the lumen which surround it. One factor impeding the success of stent technology in endoluminal treatments is the frequent occurrence of in-stent restenosis, characterized by proliferation and migration of smooth muscle cells within and/or adjacent to the implanted stent, causing reclosure or blockage of the body lumen.

Atherosclerosis and restenosis can be treated in a variety of ways, including drugs, bypass surgery, and a variety of catheter-based approaches which rely on intravascular debulking or removal of the atheromatous or other material occluding a blood vessel. Of particular interest to the present invention, a variety of methods for cutting or dislodging material and removing such material from the blood vessel have been proposed, generally being referred to as atherectomy procedures. Atherectomy catheters intended to excise material from the blood vessel lumen generally employ a rotatable and/or axially translatable cutting blade which can be advanced into or past the occlusive material in order to cut and separate such material from the blood vessel lumen. In particular, side-cutting atherectomy catheters generally employ a housing having an aperture on one side, a blade which is rotated or translated by the aperture, and a balloon to urge the aperture against the material to be removed.

Although atherectomy catheters have proven very successful in treating many types of atherosclerosis and in-stent restenosis, improved atherectomy catheters and methods are continuously being pursued. For example, many currently available side-cutting atherectomy catheters have difficulty in capturing occluding material in the cutting aperture. To facilitate material capture, the cutting aperture is frequently elongated to increase the area into which the material can penetrate. Such elongation typically requires an equivalent lengthening of the cutter housing. Since most cutter housings are rigid, such lengthening makes it more difficult to introduce the distal end of the catheter through tortuous regions of the vasculature.

Another shortcoming of many currently available atherectomy catheters is that they typically require a balloon positioned opposite the cutting window to urge the cutting window into contact with occluding material. Such balloons, however, unduly increase the size of the distal portion of the catheter. Even with the balloon, the amount of material that can be removed by conventional atherectomy catheters is limited by the size of the cutting window. Other disadvantages of some catheters include cutting elements with less than ideal hardness, inadequate storage space within the catheter for containing removed material, sub-optimal guide wire lumens, and/or the like. In addition, the available atherectomy catheters generally provide material insufficient in quantity and/or quality for testing by many histological, array, proteomic or other biochemical or molecular methods. For example, in one report a device and method available to the artisan collected less than about 50 mg of tissue. (Safian et al., *Circulation* 82:305-307 (1990)). This amount of material is not typically enough to carry out more than one test, or is insufficient to successfully carry out a number of diagnostic tests available to the physician or researcher.

For these reasons, it would be advantageous to have atherectomy catheters which could access small, tortuous regions of the vasculature and remove atheromatous and other occluding materials from within blood vessels and stents in a controlled fashion. In particular, it would be desirable to have atherectomy catheters which could facilitate capturing and invagination of atheromatous materials. Particularly, those capable of in vivo capturing and removing at least one continuous tissue strand of sufficient quantity and quality for testing in vitro. Ideally, such catheters and methods for their use would be adaptable for use in a variety of body lumens, including but not limited to coronary and other arteries. At least some of these objectives will be met by the present invention.

BRIEF SUMMARY OF THE INVENTION

The present invention provides catheters for removing material from (or "debulking") a body lumen. Catheters of the present invention may be used in a variety of body lumens, including but not limited to intravascular lumens such as coronary arteries. Typically, debulking catheters are used to remove occlusive material, such as atherosclerotic plaque, from vascular lumens, but they may alternatively be used to remove other materials. Generally, debulking catheters include a proximal portion, a distal portion having a window, and a tissue debulking assembly which may be exposed through the window to contact material in a body lumen. The catheter debulks a body lumen when it is moved while the tissue debulking assembly is in contact with the material in the lumen.

Catheters of the present invention are configured to enhance the removal of occlusive material from a body lumen by providing catheters with one or more improved features. For example, some embodiments include a deflected or deflectable portion of the catheter, such as a distal portion that is deflectable relative to the proximal portion or a deflected or deflectable section near the distal end of the proximal portion. Such deflection may help to urge a portion of the catheter into contact with material adhered to the sidewall of a body lumen to facilitate removal of the material. Deflection may also expose the tissue debulking assembly through the window on the catheter body. In various embodiments, other advantageous features of the catheters of the present invention include, but are not limited to, telescoping guidewire lumens, a shuttle mechanism for locking the tissue debulking assembly in a given position, debulking assemblies having improved materials and shapes, imaging devices, improved material storage tips and the like.

In one aspect of the present invention, a debulking catheter for removing material from a body lumen includes a catheter body and a tissue debulking assembly. The catheter body generally includes a proximal portion and a distal portion, with the distal portion having a window. The tissue debulking assembly is disposed at least partially within the distal portion of the catheter body and is radially movable to expose at least a portion of the assembly through the window to contact the material in the body lumen. The tissue debulking assembly itself may take any of a number of suitable forms, but in one embodiment it comprises a rotatable cutter. Optionally, such a cutter may include a beveled edge for contacting the material in the body lumen while preventing injury to the body lumen. In some embodiments, the cutter includes a tungsten carbide cutting edge for improved durability and cutting ability. In still other embodiments, the tissue debulking assembly may comprise a radio frequency electrode, a laser, an ultrasound emitter and/or the like.

Catheters of the present invention may have many various sizes and configurations. In one embodiment, for example, the distal portion has an outer diameter of between about 0.1 cm and about 0.22 cm and the window has a length of between about 0.12 cm and about 0.25 cm. The proximal portion and the distal portion of the catheter body typically define a channel having a longitudinal axis. In embodiments including a rotatable cutter, the catheter may optionally further include a drive shaft positioned within this channel, with the drive shaft being attachable to a driver for rotating the cutter.

Optionally, the distal portion of the catheter may angularly deflect, relative to the proximal portion. In some embodiments, such deflection urges a portion of the catheter against material in a body lumen. For example, the window of the catheter body may be urged against the material. In other embodiments, deflection of the distal portion relative to the proximal portion exposes a portion of the tissue debulking assembly through the window to contact material in a body lumen. In some embodiments, deflection will both urge the window against the material and expose the tissue debulking assembly through the window. Often, the distal portion deflects in a direction opposite of the window about an axis that is substantially orthogonal to the longitudinal axis of the catheter body. For example, the distal portion may be coupled to the proximal portion with a joint, with movement of the tissue debulking assembly actuating deflection of the distal portion about the joint. In embodiments with such joints, the catheter may optionally include a ramp positioned on the distal portion of the catheter opposite of the window, with proximal movement of the tissue debulking assembly over the ramp deflecting the distal portion to expose the tissue debulking assembly out of the window and into contact with material in the lumen. Also optionally, such a catheter may include a tissue debulking assembly having a shuttle mechanism to lock the debulking assembly in place when the distal portion is deflected. Such shuttle mechanisms may be coupled with the proximal portion of the catheter body by means of a first joint and with the distal portion of the body by means of a second joint, so that the shuttle mechanism is movable relative to the distal portion, the proximal portion or both.

In some embodiments of the invention, the tissue debulking assembly is movable between a first position and a second position, with the tissue debulking assembly in the first position closing the window. Optionally, the movable tissue debulking assembly in the second position may extend beyond an outer diameter of the distal portion of the catheter body. For example, in some embodiments the debulking assembly in the second position extends beyond the outer diameter of the distal portion by between about 0.025 mm and about 0.64 mm. In some embodiments, the tissue debulking assembly in the second position moves a longitudinal axis of the assembly to an angled position relative to the longitudinal axis of the distal portion and out of the window beyond the outer diameter of the distal portion. Alternatively, the tissue debulking assembly in the second position may move a longitudinal axis of the assembly to an offset parallel position relative to the longitudinal axis of the distal portion and out of the window beyond the outer diameter of the distal portion.

Some embodiments of the invention have a proximal portion further including at least one rigid portion disposed near a distal end of the proximal portion for helping to urge the tissue debulking assembly into the material in the body lumen. For example, the rigid portion may comprise a curvature in the proximal portion of the catheter body, near the distal end of the proximal portion. In other embodiments, the rigid portion comprises a length of the proximal portion of the catheter body in which a first side of the proximal portion is less rigid than a second side, wherein the first and second sides are disposed opposite one another across a cross section of the rigid portion so that tension applied to the proximal portion in the proximal direction causes the catheter body to deflect in the direction of the first side. The second side would typically be disposed opposite the side of the window so that tension applied to the proximal portion in the proximal direction causes the window to be urged into contact with the material in the body lumen.

Optionally, catheters of the invention may include a flexible distal tip coupled to the distal portion, with at least one of the distal tip and distal portion comprising a collection chamber for removed material. In some embodiments, the collection chamber is at least partially translucent and the distal portion adjacent the window is radiopaque, to enhance visualization of the window, relative to the chamber. In some embodiments, the distal tip comprises the collection chamber, and the distal tip and the distal portion have complementary interlocking components for attaching with one another.

Some embodiments will include one or more guidewire lumens. For example, some embodiments include a proximal guidewire lumen coupled with the proximal portion of the catheter body and a distal guidewire lumen coupled with at least one of the distal tip and the distal portion of the catheter body. Where separate guidewire lumens are used, a distal guidewire lumen may have any suitable length such as between about 2.0 cm and about 3.0 cm. Similarly, the proximal guidewire lumen may have any suitable length, such as between about 10 cm and about 14 cm.

In another embodiment, a catheter includes a proximal guidewire lumen coupled with the proximal portion and a distal telescoping guidewire lumen coupled with at least one of the distal tip and the distal portion and extending within the proximal guidewire lumen to form a continuous guidewire lumen. Generally, the distal telescoping guidewire lumen is movable in and out of the proximal guidewire lumen upon deflection of the distal portion of the catheter relative to the proximal portion. In these embodiments, the telescoping distal lumen may be longer that the distal lumens described previously. For example, the distal guidewire lumen may have a length of between about 5.0 cm and about 8.0 cm and the proximal guidewire lumen may have a length of between about 10 cm and about 14 cm, in various embodiments. Often, in embodiments including a distal telescoping lumen, a portion of the distal guidewire lumen is not attached to the catheter body.

In another aspect of the invention, a rapid exchange debulking catheter for removing material from a body lumen includes an elongate catheter body, a tissue debulking assembly, a proximal guidewire lumen and a distal telescoping guidewire lumen. The elongate catheter body generally comprises an articulable distal portion coupled to a proximal portion. The tissue debulking assembly is coupled to the articulable distal portion for removing the material from the body lumen. The proximal guidewire lumen coupled to the proximal portion, and the distal telescoping guidewire lumen is at least partially coupled with the distal portion and extends within the proximal guidewire lumen to form a continuous guidewire lumen. Generally, the rapid exchange debulking catheter may include any of the features described about in relation to catheters of the present invention.

Optionally, the elongate catheter body comprises an inner lumen that extends through the proximal portion and the distal portion, and the tissue debulking assembly is positioned within the inner lumen. In some embodiments, the proximal guidewire lumen and a portion of the distal guidewire lumen are attached to an outer surface of the inner lumen. In many embodiments including the distal telescoping guidewire lumen, a portion of the distal guidewire lumen is not attached to the catheter body. Typically, the unattached portion is positioned adjacent the debulking assembly. The rapid exchange debulking catheter may optionally include a guidewire that extends through the continuous guidewire lumen. Typically, the guidewire enters a proximal port of the proximal guidewire lumen, runs through the continuous guidewire lumen, and exits a distal port of the distal guidewire lumen.

In some embodiments, the elongate catheter body comprises a central axis that runs through the proximal portion and the articulable distal portion, with the articulable distal portion being deflectable off of the central axis relative to the proximal portion.

In another aspect of the present invention, a method of removing material from a body lumen includes delivering a catheter comprising a tissue debulking assembly coupled with a drive shaft to a target site in the body lumen and moving the drive shaft to expose the tissue debulking assembly and deflect a distal portion of the catheter relative to a proximal portion of the catheter. In some embodiments, moving the drive shaft comprises actuating a single input device.

Optionally, the tissue debulking assembly may comprise a rotatable cutter. In those embodiments, actuating the single input device may further include rotating the tissue debulking assembly. The rotatable cutter, for example, may include a beveled edge for contacting the material in the body lumen while preventing injury to the body lumen. In some embodiments, the rotatable cutter may include a tungsten carbide cutting edge. Optionally, the proximal portion and the distal portion may define a channel having a longitudinal axis, the drive shaft positioned within the channel, wherein the drive shaft is attachable to a driver for rotating the cutter.

In some embodiments, moving the drive shaft to deflect the distal portion urges a window on the catheter against material in the body lumen. Also in some embodiments, moving the drive shaft deflects the distal portion in a direction opposite of a window on the catheter about an axis that is substantially orthogonal to a longitudinal axis of the catheter body. Optionally, moving the drive shaft may actuate deflection of the distal portion about a joint. In some embodiments, moving the drive shaft further comprises moving the tissue debulking assembly over a ramp in the catheter to deflect the distal portion and to expose the tissue debulking assembly out of a window to contact material in the body lumen. Moving the drive shaft may even further comprise locking the tissue debulking assembly in place via a shuttle mechanism when the distal portion is deflected. The shuttle mechanism may be coupled with the proximal portion by means of a first joint and with the distal portion by means of a second joint, so that the shuttle mechanism is movable relative to the distal portion, the proximal portion or both.

The present further provides methods for excising and testing material from a body lumen. The method can comprise the steps of i) providing a catheter having a rotating cutter, a collection chamber, and a cutting window, the rotating cutter being movable between a stored position and an exposed position, at least part of the rotating cutter becoming exposed through the cutting window when moving to the exposed position, ii) the exposing of the cutter by moving the cutter to the exposed position, iii) advancing the catheter to move the rotating cutter through material in a first site in the body lumen, the rotating cutter remaining in the exposed position so that the cutter and the window maintain their orientation with respect to one another when advancing the catheter through the material, the material cut by the rotating cutter being directed through the cutting window and into the collection chamber as the catheter is advanced through the material, iv) removing the material from the collection chamber, and performing one or more tests on at least a portion of the material removed from the collection chamber. In certain embodiments of the method, the material collected can be placed in a preserving agent, tissue fixative, or a preparation agent prior to testing.

The methods disclosed for the collection of material from the body lumen provides a continuous strip of tissue that can be longer than the cutting window. This material can provide sufficient amount of sample material of a quality and quantity that can be used for one or more of genomic screening, DNA hybridization, RNA hybridization, gene expression analysis, PCR amplification, proteomic testing, drug efficacy screening, a presence of one or more protein markers, a presence of one or more DNA markers, a presence of one or more RNA markers, histological testing histopathology, cytopathology, call and tissue type analysis, biopsy, or the like. In addition the material collected can be sufficient in amount and quality for testing for one or more of the presence of DNA, RNA, or a protein marker comprising a smooth muscle proliferative promoter, a smooth muscle proliferative inhibitor, a cellular marker, an apoptotic marker, a cell cycle protein, a transcriptional factor, a proliferative marker, an endothelial growth factor, an adhesion molecule, a cytokine, a chemokine receptor, an inflammation marker, a coagulation factor, a fibrinolytic factor, an oxidative stress related molecule, an extracellular matrix molecule, an interleukin, a growth factor, a glycoprotein, a proteoglycan, a cell-surface marker, a serum marker, or an immune factor. In certain embodiments the amount of material can be about 1 mg to about 2000 mg, more typically the amount of material can be about 1 mg to about 100, mg, about 100 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, or about 800 mg up to about 2000 mg. The material can be collected in a single access or can be collected in multiple transluminal access in the same patient.

In a certain embodiment of the present invention the method can comprise prior to removing the material from the collection chamber the steps of i) moving the cutter to the stored position, ii) repositioning the catheter at a second site, iii) exposing the cutter by moving the cutter to the exposed position, and iv) advancing the catheter to move the rotating cutter through material in the second site, the rotating cutter remaining in the exposed position so that the cutter and the window maintain their orientation with respect to one another when advancing the catheter through the material, the material cut by the rotating cutter being directed through the cutting window and into the collection chamber as the catheter is advanced through the material. The first and second sites can be in the same of different body lumens.

In certain particular embodiments of the present invention discloses a method for removing material from a vascular location comprising the steps of i) providing a catheter having a body, an opening leading to a collection chamber, and a cuter, the cutter being movable between a stored position and an exposed position, the cutter becoming at least partially exposed when moving from the stored position to the exposed position, ii) introducing the catheter into a patient's vascular system with the cutter in the stored position, the catheter being introduced to the vascular location where material is to be removed, iii) exposing the cutter by moving the cutter to the exposed position, iv) rotating the cutter, v) advancing the catheter after the exposing step and during the rotating step, wherein the rotating cutter and the opening advance together so that material cut by the rotating cutter is directed through the opening and into the collection chamber as the catheter is advanced, vi) removing the catheter from the vascular location, vii) harvesting the material from the collection chamber after the catheter has been removed in vivo from the vascular location; and viii) performing at least one or more tests on at least a portion of the material removed from the collection chamber. The method can be used to collect at least about 1 mg to about 2000 mg, more typically the amount of material can be about 1 mg to about 100, mg, about 100 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, or about 800 mg up to about 2000 mg. Due to the large amount of material harvested, the physician will have the option of repeat testing or validation testing, as needed.

Prior to testing the harvested material, the material can be placed in a preserving agent, a tissue fixative, or a preparation agent compatible with a particular test to be run. The material can be collected in a single access or can be collected in multiple transluminal access in the same patient. Further the material is typically at least one substantially consistent, continuous strip of material that maintains the heterogeneous structure of the material as it was removed from the inner surface of the lumen of the patient. Also, each strip of material can be collected from at least a first site or from the first site and a second or additional site from the same or a different body lumen.

The present invention also provides the opportunity for selective plaque excision, a process that targets highly specific diseased areas, as opposed to previous treatments which could not discriminate between unhealthy and healthy areas and thus resulted in a blend of diseased and non-diseased tissue to analyze.

For a further understanding of the nature and advantages of the invention, reference should be made to the following description taken in conjunction with the accompanying drawings.

BRIEF DESCRIPTION OF THE DRAWINGS

FIGS. 3C and 3D are views of the distal portion of a debulking catheter, where the distal portion has a locking shuttle mechanism;

FIGS. 4C and 4D are views of the distal portion of a debulking catheter, where the distal portion has a locking shuttle mechanism;

FIG. 5A is an end view of the distal portion of the debulking catheter of FIG. 1 in which the cutter is in a packing position within a tip of the catheter;

FIG. 5B is a sectional view along Line A-A of FIG. 5A;

FIG. 9A is a perspective view of a cutter of the present invention;

FIG. 9B is an end view of the cutter of FIG. 9A;

FIG. 9C is a sectional view of the cutter along Line A-A of the cutter of FIGS. 9A and 9B;

FIG. 10A is a perspective view of a in-stent restenosis cutter of the present invention;

FIG. 10B is an end view of the cutter of FIG. 10A;

FIG. 10C is a sectional view of the cutter along Line B-B of the cutter of FIGS. 10A and 10B;

FIG. 23 shows the weight and lengths of 20 fragments of vascular material excised according to the present invention.

FIG. 24 shows relevant markers for which the excised vascular material can be tested for expression

DETAILED DESCRIPTION OF THE INVENTION

Figure 1:
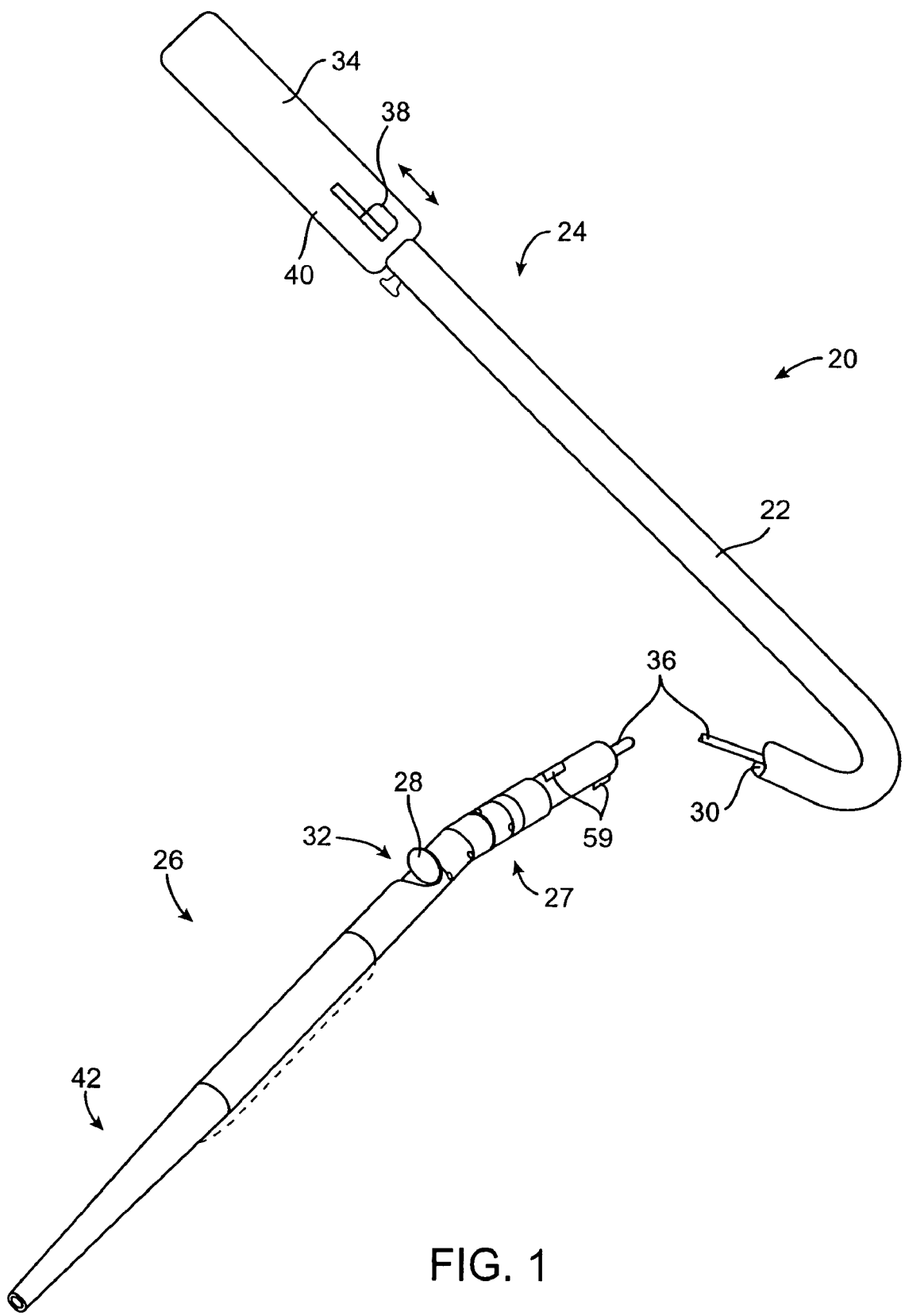
FIG. 1 is a perspective view of a debulking catheter of the present invention.

The catheters and methods of the present invention are designed to debulk atheroma and other occlusive material from diseased body lumens, and in particular coronary arteries, de novo lesions, and in-stent restenosis lesions. The catheters and methods, however, are also suitable for treating stenoses of body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Debulking of such material can thus be beneficial to maintain patency of the body lumen. The catheters and methods of the present invention also provide methods that provide lumenectomy samples or materials that are of higher quality and quantity that typically have been provided by prior devices. The material provided is typically a continuous strip of tissue removed from the lumen interior wall that ranges from about 1 mg to about 2000 mg and wherein the tissue retains the structure of the tissue prior to removal. Advantageously, the continuous strip or strand of tissue removed will typically have a length that is longer than a length of the cutting window. While the remaining discussion is directed at debulking and passing through atheromatous or thrombotic occlusive material in a coronary artery, it will be appreciated that the systems and methods of the present invention can be used to remove and/or pass through a variety of occlusive, stenotic, or hyperplastic material in a variety of body lumens.

Apparatus according to the present invention will generally comprise catheters having catheter bodies adapted for intraluminal introduction to the target body lumen. The dimensions and other physical characteristics of the catheter bodies will vary significantly depending on the body lumen which is to be accessed. In the exemplary case of atherectomy catheters intended for intravascular introduction, the proximal portions of the catheter bodies will typically be very flexible and suitable for introduction over a guidewire to a target site within the vasculature. In particular, catheters can be intended for "over-the-wire" introduction when a guidewire channel extends fully through the catheter body or for "rapid exchange" introduction where the guidewire channel extends only through a distal portion of the catheter body. In other cases, it may be possible to provide a fixed or integral coil tip or guidewire tip on the distal portion of the catheter or even dispense with the guidewire entirely. For convenience of illustration, guidewires will not be shown in all embodiments, but it should be appreciated that they can be incorporated into any of these embodiments.

Catheter bodies intended for intravascular introduction will typically have a length in the range from 50 cm to 200 cm and an outer diameter in the range from 1 French to 12 French (0.33 mm: 1 French), usually from 3 French to 9 French. In the case of coronary catheters, the length is typically in the range from 125 cm to 200 cm, the diameter is preferably below 8 French, more preferably below 7 French, and most preferably in the range from 2 French to 7 French. Catheter bodies will typically be composed of an organic polymer which is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, often the coronary arteries, by conventional techniques.

The distal portion of the catheters of the present invention may have a wide variety of forms and structures. In many embodiments, a distal portion of the catheter is more rigid than a proximal portion, but in other embodiments the distal portion may be equally as flexible as the proximal portion. One aspect of the present invention provides catheters having a distal portion with a reduced rigid length. The reduced rigid length can allow the catheters to access and treat tortuous vessels and small diameter body lumens. In most embodiments a rigid distal portion or housing of the catheter body will have a diameter that generally matches the proximal portion of the catheter body, however, in other embodiments, the distal portion may be larger or smaller than the flexible portion of the catheter.

A rigid distal portion of a catheter body can be formed from materials which are rigid or which have very low flexibilities, such as metals, hard plastics, composite materials, NiTi, steel with a coating such as titanium nitride, tantalum, ME-92®, diamonds, or the like. Most usually, the distal end of the catheter body will be formed from stainless steel or platinum/iridium. The length of the rigid distal portion may vary widely, typically being in the range from 5 mm to 35 mm, more usually from 10 mm to 25 mm, and preferably between 6 mm and 8 mm. In contrast, conventional catheters typically have rigid lengths of approximately 16 mm.

The side opening windows of the present invention will typically have a length of approximately 2 mm. In other embodiments, however, the side opening cutting window can be larger or smaller, but should be large enough to allow the cutter to protrude a predetermined distance that is sufficient to debulk material from the body lumen.

The catheters of the present invention can include a flexible atraumatic distal tip coupled to the rigid distal portion of the catheter. For example, an integrated distal tip can increase the safety of the catheter by eliminating the joint between the distal tip and the catheter body. The integral tip can provide a smoother inner diameter for ease of tissue movement into a collection chamber in the tip. During manufacturing, the transition from the housing to the flexible distal tip can be finished with a polymer laminate over the material housing. No weld, crimp, or screw joint is usually required.

The atraumatic distal tip permits advancing the catheter distally through the blood vessel or other body lumen while reducing any damage caused to the body lumen by the catheter. Typically, the distal tip will have a guidewire channel to permit the catheter to be guided to the target lesion over a guidewire. In some exemplary configurations, the atraumatic distal tip comprises a coil. In some configurations the distal tip has a rounded, blunt distal end. The catheter body can be tubular and have a forward-facing circular aperture which communicates with the atraumatic tip. A collection chamber can be housed within the distal tip to store material removed from the body lumen. The combination of the rigid distal end and the flexible distal tip is approximately 30 mm.

A rotatable cutter or other tissue debulking assembly may be disposed in the distal portion of the catheter to sever material which is adjacent to or received within the cutting window. In an exemplary embodiment, the cutter is movably disposed in the distal portion of the catheter body and movable across a side opening window. A straight or serrated cutting blade or other element can be formed integrally along a distal or proximal edge of the cutting window to assist in severing material from the body lumen. In one particular embodiment, the cutter has a diameter of approximately 1.14 mm. It should be appreciated however, that the diameter of the cutter will depend primarily on the diameter of the distal portion of the catheter body.

In exemplary embodiments, activation of an input device can deflect a distal portion of the catheter relative to the proximal portion of the catheter. Angular deflection of the distal portion may serve one or more purposes in various embodiments. Generally, for example, deflection of the distal portion increases the effective "diameter" of the catheter and causes the debulking assembly to be urged against material in a lumen, such as, but not limited to, atherosclerotic plaque. In other embodiments, deflection of the distal portion may act to expose a debulking assembly through a window for contacting material in a lumen. In some embodiments, for example, activation of the input device moves the debulking assembly over a ramp or cam so that a portion of the rigid distal portion and flexible tip are caused to drop out of the path of the debulking assembly so as to expose the debulking assembly through the window. In some embodiments, deflection may both urge a portion of the catheter into material in a lumen and expose a tissue debulking assembly.

It should be understood movement of a tissue debulking assembly may cause deflection of a portion of the catheter or that deflection of the catheter may cause movement or exposure of a tissue debulking assembly, in various embodiments. In other embodiments, deflection of a portion of the catheter and movement of the tissue debulking assembly may be causally unconnected events. Any suitable combination of deflecting, exposing of a debulking assembly and the like is contemplated. In carrying out deflection, exposure and/or the like, a single input device may be used, so that a user may, for example, deflect a portion of a catheter and expose a tissue debulking assembly using a single input device operable by one hand. In other embodiments, rotation of a tissue debulking assembly may also be activated by the same, single input device. In other embodiments, multiple input devices may be used.

Some embodiments further help to urge the debulking assembly into contact with target tissue by including a proximal portion of the catheter body having a rigid, shaped or deformable portion. For example, some embodiments include a proximal portion with a bend that urges the debulking assembly toward a side of the lumen to be debulked. In other embodiments, one side of the proximal portion is less rigid than the other side. Thus, when tension is placed on the catheter in a proximal direction (as when pulling the debulking assembly proximally for use), one side of the proximal portion collapses more than the other, causing the catheter body to bend and the debulking assembly to move toward a side of the lumen to be debulked.

In exemplary embodiments, the debulking assembly comprises a rotatable cutter that is movable outside the window. By moving the cutter outside of the cutting window beyond an outer diameter of the distal portion of the catheter, the cutter is able to contact and sever material that does not invaginate into the cutting window. In a specific configuration, the rotating cutter can be moved over the cam within the rigid, or distal, portion of the catheter body so that the cutting edge is moved out of the window. Moving the rotating cutter outside of the cutting window and advancing the entire catheter body distally, a large amount of occlusive material can be removed. Consequently, the amount of material that can be removed is not limited by the size of the cutting window.

Certain embodiments of the present invention provide for methods for in vivo excising and removing material from the inner wall of one or more lumen that is of higher quantity and quality than prior devices or methods. The material removed therefore is better suited for use in various testing methods. Particularly, the methods provide sufficient material or better quality and quantity for use in one or more tests from a single percutaneous translumenal lumenectomy procedure. Further, the material typically maintains the structure possessed by the material in vivo. This provides for the ability to carry out certain tests, such as histology, cytopathology, and other tests that have been difficult to perform using prior devices and methods.

In one embodiment the method of the present invention for excising and testing material from a body lumen comprises the steps of providing a catheter having a rotating cutter, a collection chamber, and a cutting window, the rotating cutter being movable between a stored position and an exposed position, at least part of the rotating cutter becoming exposed through the cutting widow when moving to the exposed position. The catheter is advanced transluminally through the body lumen to move or plane the rotating cutter through material in a first site in the body lumen, the rotating cutter remaining in the exposed position so that the cutter and the widow maintain their orientation with respect to one another when advancing the catheter and planing through the material. The planing action of the present invention provides a substantially consistent and even tissue removal through the body lumen. The continuous strand of material cut by the rotating cutter is directed through the cutting widow and into the collection chamber as the catheter is advanced through the material. The material can then be removed from the collection chamber and one or more tests performed on at least a portion of the material removed from the collection chamber.

The material or tissue excised from the body lumen will vary in length and will depend on the catheter configuration, the type of material removed, the body lumen, and the like. However, in certain embodiments, the material will be in the form of continuous strands that has a substantially consistent depth and width of tissue cuts. The material is typically longer than the length of the cutting window (but it may be shorter), and typically has a length of about 2.0 mm or longer, and sometimes between about 0.5 cm up to about 10 cm or longer in length. Typically the length of a continuous strand is at least 2 cm, at least 5 cm, at least 7 cm, at least 10 cm, or at least 15 cm. The length of a strand is the dimension which is axial to the lumen. Advantageously, the planing action of the catheter provides a material tissue structure that reflects the actual in vivo tissue structure, and provides information about larger portions of the disease state of the body lumen. One or more strands may be obtained from a single vascular lumen or single vascular obstruction. Because of the design and configuration of the device, the strands typically have a depth of at least 0.1 mm, at least 0.25 mm, at least 0.33 mm, or at least 0.5 mm. Depth of a strand is the dimension which is radial to the axis of a lumen. The cutting and planing action of the device of the invention achieves large volumes which are excellent for analysis, for multiple analyses, for storage as archival samples, and for assembly into libraries of samples representative of certain disease states. The mass/length ratio of continuous strands is typically at least 0.45 mg/mm, at least 0.50 mg/mm, at least 0.55 mg/mm, at least 0.60 mg/mm, at least 0.65 mg/mm, or at least 0.70 mg/mm. Libraries of samples can be assembled for studies of drugs, candidate drugs, toxins, therapeutic treatments, etc. The samples can be preserved according to any method known in the art. Samples may be frozen, for example, in liquid nitrogen, they may be preserved in paraffin, dried, freeze dried, etc. Samples may be treated to achieve a purified or semi-purified component of the sample. Samples may be treated, for example to extract DNA or protein. Samples may be treated to extract mRNA and to preserve it or "convert" it to cDNA. Desirably, samples are stored in a systematic way so that patient information remains associated with the samples and patient outcome can be associated with the sample concurrently or at a later time.

Tissue retrieved via the present invention provides an opportunity for greater confidence in test results for single or multiple tests due to reduced sampling errors resulting from greater tissue volume and enhanced tissue quality than was previously possible. Previously, the retrieved atherectomized tissue samples had problems because there was only angiographic control possible for the evaluation of how much stenotic tissue has been sampled. With the present invention, it is more confidently known how much stenotic tissue is sampled with a retrieval. Generally, the smooth muscle cells of the stenotic material show a range of phenotypes, but most of the cells contained myofilaments as well as a relatively high amount of synthetic organelles, such as rough endoplasmic reticulum, Golgi apparatus and mitochondria. A larger tissue sample of better quality and more confidence in the retrieval location can help determine with confidence how much stenotic tissue is retrieved in the procedure. Because the absence of inflammatory cells in excised tissue may be only one of many variables in sorting out a cardiovascular condition, the presence of the inflammatory cells within critical areas of plaque may be more important than their sheer number. Using the methods of the present invention, the location and degree of inflammatory cells present may be determined in order to facilitate a more informed diagnosis.

In the past, there has been difficulty obtaining sufficient plaque or other material to perform proliferation studies and to sub-cultivate tissue. The problem associated with the inability to obtain fresh human plaque tissue is underscored by the significant need for a tissue model wherein smooth muscle cells can be analyzed with as many of the original characteristics attributed to the previous in vivo injury as possible. Sufficient tissue of good quality will obviate the need to cultivate these cells. To date it has not been possible to directly compare smooth muscle cells from restenotic and primary lesions, a comparison that could be facilitated using primary and restenotic tissue retrieved by the present invention.

The material removed from the collection chamber, or a portion thereof, can be placed in a preserving agent, a tissue fixative, and or a preparation agent suitable for a desired test prior to testing the material. The material removed from the patient by this method is typically at least one or more continuous strip(s) of material that maintains the structure of the material in vivo. The quantity of material removed by the method can be from about 1 mg to about 2000 mg. Typically the amount of material is about 1 mg to about 100 mg, about 100 mg to about 200 mg, about 200 mg to about 300 mg, 300 mg to about 400 mg, 400 mg to about 500 mg, 500 mg to about 600 mg, about 600 mg to about 700 mg, 700 mg to about 800 mg, or about 800 mg to about 2000 mg. In a typical procedure about 400 mg to about 600 mg of material is removed and available for testing and/or storage. A preferred embodiment of the present invention provides for the collection of one or more continuous strips of material from the inner surface of the lumen that is longer than a largest dimension of the cutting window. In a particular example, the material can comprise plaque tissue.

The methods of the present invention provide high quality material is a sufficient quantity that allows for multiple testing methods (e.g., validation testing, repeat testing, etc.) and provides a sufficient amount of sample to allow storage of an amount of sample to allow later confirmatory or additional testing to confirm a diagnosis without having to subject the patient to another percutaneous translumenal lumenectomy procedure. The methods can provide sufficient high quality material for tests comprising genomic screening, DNA hybridization, RNA hybridization, gene expression analysis, PCR amplification, proteomic testing, drug efficacy screening, a presence of one or more protein markers, a presence of one or more DNA markers, a presence of one or more RNA markers, histological testing, histopathology, cytopathology, cell and tissue type analysis, biopsy, and the like. Additionally, the material can also be cultured to determine reactivity to drugs, e.g., therapeutic drugs, and the like. Being able to carry out such testing provides for the ability to perform one or more tests comprising, for example, but not limitation, analyzing the material for the presence of DNA, RNA, or a protein marker comprising a smooth muscle proliferative promoter, a smooth muscle proliferative inhibitor, a cellular marker, an apoptotic marker, a cell cycle protein, a transcriptional factor, a proliferative marker, an endothelial growth factor, an adhesion molecule, a cytokine, a chemokine, a chemokine receptor, an inflammation marker, a coagulation factor, a fibrinolytic factor, an oxidative stress related molecule, an extracellular matrix molecule, an interleukin, a growth factor, a glycoprotein, a proteoglycan, a cell-surface marker, a serum marker, and or an immune factor, and the like. Markers can include peptides or polypeptide markers as well as protein markers. Tests for each of these molecules and others are well known to the skilled artisan as are methods and preservatives, fixatives and preparation agents for adding to all or a portion of the material collected.

In another embodiment of the present invention the method can further comprise i) moving the cutter to the stored position, ii) repositioning the catheter at a second site, iii) exposing the cutter by moving the cutter to the exposed position, and iv) advancing the catheter to move the rotating cutter through material in the second site, the rotating cutter remaining in the exposed position so that the cutter and the widow maintain their orientation with respect to one another when advancing the catheter through the material, the material cut by the rotating cutter being directed through the cutting widow and into the collection chamber as the catheter is advanced through the material. The first and second sites can be in either the same or a different body lumen.

Another embodiment of the methods of the present invention for removing material from a vascular location comprises the steps of providing a catheter having a body, an opening leading to a collection chamber, and a cutter, the cutter being movable between a stored position and an exposed position, the cutter becoming at least partially exposed when moving from the stored position to the exposed position. The catheter is then percutaneously introduced into and transluminally advanced through a patient's vascular system with the cutter in the stored position, the catheter being introduced into the vascular location where material is to be removed. The cutter is then exposed by moving the cutter to the exposed position and the cutter is rotated. The catheter is then advanced after the exposing step and during the rotating step, wherein the rotating cutter and the opening advance together so that material cut by the rotating cutter is directed through the opening and into the collection chamber as the catheter is advanced. Subsequent to excising the material the catheter is removed from the vascular location and the material collected in the collection chamber is harvested and one or more tests on at least a portion of the material removed from the collection chamber can be carried out.

The material removed from the collection chamber, or a portion thereof, can be placed in a preserving agent, a tissue fixative, and or a preparation agent suitable for a desired test prior to testing the material. The material removed from the patient by this method is typically at least one or more continuous strip(s) of material that maintains the structure of the material in vivo. The quantity of material removed by the method can be from about 1 mg to about 2000 mg. Typically the amount of material is about 1 mg to about 100 mg, about 100 mg to about 200 mg, about 200 mg to about 300 mg, 300 mg to about 400 mg, 400 mg to about 500 mg, 500 mg to about 600 mg, about 600 mg to about 700 mg, 700 mg to about 800 mg, or about 800 mg to about 2000 mg. In a typical procedure about 400 mg to about 600 mg of material is removed and available for testing and/or storage. A preferred embodiment of the present invention provides for the collection of one or more continuous strips of material from the inner surface of the lumen that is longer than a largest dimension of the cutting window. In a particular example, the material can comprise plaque tissue. The material can be collected from a single site or at least one additional site in the same or a different body lumen.

The material produced by the methods of the invention provide a lumenectomy composition comprising at least one continuous tissue stand collected in vivo from an inner surface of the body lumen of a subject. In one embodiment the body lumen can be an artery or other lumen or vessel of the circulatory system and the material can comprise arterial plaque and associated tissue. The continuous stand of tissue provided by the disclosed methods provide a sufficient amount of high quality material to successfully perform at least one or more tests comprising, for example, genomic screening, DNA hybridization, RNA hybridization, gene expression analysis (including serial analysis of gene expression), PCR amplification, proteomic testing, drug efficacy screening, a determination of the presence of one or more protein markers, a determination of the presence of one or more DNA markers, a determination of the presence of one or more RNA markers, histological testing, histopathology, cytopathology, cell type analysis, tissue type analysis, biopsy, and the like. Methods for performing each of the tests are well known to the skilled artisan. It is also well known that material collected from a patient can be added to a preserving agent, tissue fixative, or a preparation agent in order to prepare at least a portion of collected material for the desired test. Agents known in the art for preserving, fixing or preparing the material for later use include, for example, saline, heparinized saline, liquid nitrogen, formalin, a membrane lysis agent, a RNA or DNA preparation agent, and the like. Particular testes that can be carried our successfully on the excised lumenectomy material removed by the methods of the present invention include, but are not limited to, histology techniques including hematoxylin and eosin staining, connective tissue staining, carbohydrate staining, and lipid staining, and the like. In addition, tissue array testing, enzyme histochemistry, transmission electron microscopy, immunohistology, immunocytochemistry, immunoassays, immunofluorescent assays, immunoprecipitation assays, ELISA, flow cytometry, fluorescent activated cell sorting, radioimmunochemistry, electrophoresis, two-dimensional gel electrophoresis, Western blotting, protein sequencing, mass spectrometry, proteomic analysis, and protein microarray analysis can be carried out. Further, cytogenetic testing, Nothern blotting, RNase protection assays, in situ hybridization assays, DNA microarray testing, reverse transcription polymerase chain reaction PCR (RT-PCR), Southern blotting, DNA sequencing, PCR amplification, single strand conformational polymorphism assays, single strand polymorphism (SNP) assays, and serial analysis of gene expression (SAGE) assays. can be successfully carried out with the lumenectomy materials compositions collected by the disclosed methods. The compositions of the present invention or portions thereof can also be prepared for storage for later testing.

In certain embodiments of the present invention the material collected can be analyzed for the presence of DNA, RNA, or protein markers comprising smooth muscle proliferative promoters (platelet-derived growth factor (PDGF), and PDGF receptor), basic fibroblast growth factor (FGF) and FGF receptor, interleukin 1 (IL-1), or transforming growth factor α (TGFα), and the like), smooth muscle proliferative inhibitors (nitric oxide/endothelial-derived relaxing factors (NO/EDRF), interferon γ (IFγ), transforming growth factor β (TGFβ), or TGFβ receptor, and the like), cellular markers (including CD68, CD3, CD4, CD8, CD20, smooth muscle actin, or CD31, and the like), apoptotic markers (Bcl-x, Bcl-2, Bax, Bak, or P53, and the like), cell cycle proteins (cyclin A, cyclin B, cyclin D, or cyclin E, and the like), transcriptional factors (transcription factor NFκB, transcription factor E2F, transcription factor CREB, or transcription factor KLF5/BTEB2, and the like), proliferative markers (Ki-67 or proliferating cell nuclear antigen (PCNA), and the like), endothelial growth factors (vascular endothelial growth factor (VEGF), and the like), adhesion molecules (intercellular adhesion molecule-1 (ICAM-1), CD11a/CD18 (LFA-1), CD11b/CD18 (MAC-1), vascular cell adhesion molecule-1 (VCAM-1), p-selectin (CD62P), or integrin, and the like), cytokines (interleukin 6 (IL-6) or interleukin 8 (IL-8), and the like), chemokines and chemokine receptors (monocyte chemoattractant protein 1 (MCP-1) and its receptor CCR2, CX3C chemokine fractalkine and its receptor CX3CR1, or eotaxin and its receptor CCR3, and the like), inflammation markers (C-reactive protein, myeloperoxidase, or complement proteins, and the like), coagulation factors and fibrinolytic factors (fibrinogen, prothrombinogen, plasminogen activator, tissue factor, or glycoprotein receptor on platelets (GpIIb-IIIa), and the like), oxidative stress related molecules (oxidized LDL and its receptor CD36, or lipoxygenase, and the like), extracellular matrix molecules (collagen, matrix metalloproteinase (MMP), FK506-binding protein 12 (FKBP12), endothelial differentiation gene receptors (EDG receptors), ephrins, elastin, lamin receptor, monocyte colony stimulating factor (M-CSF), tumor necrosis factor (TNF) or PDZ domain proteins, and the like), interleukins (interleukin 1 (IL-1), interleukin 6 (IL-6), or interleukin 8 (IL-8), and the like), growth factors (platelet-derived growth factor (PDGF), basic fibroblast growth factor (FGF), transforming growth factor α (TGFα), or transforming growth factor β (TGFβ), and the like), glycoproteins, proteoglycans (versican, hyluronan, biglycan, or deorin, and the like), cell-surface markers, serum markers, and/or immune factors (stromal cell-derived factor la (SDF-1)), and the like). Other markers that can be sought include: interleukin-18, RANTES, fractalkine, interleukin-1-beta, matrix metalloproteinase-9, tumor necrosis factor-alpha, monocyte inflammatory protein alpha, E-selectin and P-selectin. Analysis of the excised material by any of the above tests can be used for diagnosis of a condition in a patient, design a treatment directive or protocol for a subject, monitor progress of a treatment regimen, or if tests from a number of individuals are compared, the information can be used in a multi-patient analysis, such as a cardiovascular disease population study.

As will be described in detail below, in some situations it is preferable to provide a serrated cutting edge, while in other situations it may be preferable to provide a smooth cutting edge. Optionally, the cutting edge of either or both the blades may be hardened, e.g., by application of a coating. A preferred coating material is a chromium based material, available from ME-92, Inc., which may be applied according to manufacturer's instructions. In some embodiments, the cutter includes a tungsten carbide cutting edge. Other rotatable and axially movable cutting blades are described in U.S. Pat. Nos. 5,674,232; 5,242,460; 5,312,425; 5,431,673; and 4,771,774, the full disclosures of which are incorporated herein by reference. In some embodiments, a rotatable cutter includes a beveled edge for removal of material from a body lumen while preventing injury to the lumen. In still other embodiments, a tissue debulking assembly may include alternative or additional features for debulking a lumen. For example, the debulking assembly may include, but is not limited to, a radio frequency device, an abrasion device, a laser cutter and/or the like.

The catheters of the present invention may include a monorail delivery system to assist in positioning the cutter at the target site. For example, the tip of the catheter can include lumen(s) that are sized to receive a conventional guidewire (typically 0.014" diameter) or any other suitable guidewire (e.g., having diameters between 0.018" and 0.032") and the flexible proximal portion of the catheter body can include a short lumen (e.g., about 12 centimeters in length). Such a configuration moves the guidewire out of the rigid portion so as to not interfere with the debulking assembly.

In other embodiments, however, the guidewire lumen may be disposed within or outside the flexible proximal portion of the catheter body and run a longer or shorter length, and in fact may run the entire length of the flexible portion of the catheter body. The guidewire can be disposed within lumen on the flexible portion of the catheter body and exit the lumen at a point proximal to the rigid portion of the catheter. The guidewire can then enter a proximal opening in the tip lumen and exit a distal opening in the tip lumen. In some embodiments, the catheter has a distal guidewire lumen on its flexible distal tip and a proximal guidewire lumen on its flexible body. For example, in some embodiments the distal lumen may have a length of between about 2.0 cm and about 3.0 cm and the proximal lumen may have a length of between about 10 cm and about 14 cm. In yet further embodiments, a distal tip guidewire lumen may be configured to telescope within a proximal guidewire lumen, or vice versa. A telescoping guidewire lumen may enhance performance of the catheter by preventing a guidewire from being exposed within a body lumen.

The present invention may optionally employ any of a wide variety of conventional radiopaque markers, imaging devices, and/or transducers. In exemplary embodiments, the catheters of the present invention can include a radiopaque distal portion and/or radiopaque markers disposed on a distal portion of the catheter body, such as proximal and distal of the cutting window, on the cam or ramp, so as to allow the user to track the position of the cutter, or the like. The catheters of the present invention will also be particularly useful with ultrasonic transducers, such as an IVUS, of a type which may be deployed linearly within the catheter body or circumferentially on the debulking assembly. Linear deployment will allow viewing along a discrete length of the catheter axis, preferably adjacent to the cutting point, usually over a length in the range from 1 mm to 30 mm, preferably 2 mm to 10 mm. Circumferentially deployed phased arrays may subtend a viewing arc in the range from 5° to 360°, usually from 180° to 360°. For imaging transducers located on cutting blades within a housing or second cutting element, the field of imaging will generally be limited by the dimensions of the aperture. In some cases, however, it might be possible to fabricate all or a portion of the cutter blade/housing out of an ultrasonically translucent material. A more complete description of suitable imaging catheters are described more fully in U.S. patent application Ser. No. 09/378,224, filed Aug. 19, 1999, and entitled "Atherectomy Catheter with Aligned Imager," now U.S. Pat. No. 6,299,622 B1, the complete disclosure of which is incorporated herein by reference. In addition to ultrasonic array transducers, the imaging devices of the present invention may comprise optical coherence tomography devices, such as described in U.S. Pat. No. 5,491,524, the full disclosure of which is incorporated herein by reference, as well as Huang et al. (1991) Science 254:1178-1181; Brezinski et al. (1997) Heart 77:397-403; and Brezinski et al (1996) Circulation 93:1206-1213. In some instances, the present invention may also provide optical imaging using optical wave guides and the like.

Referring now to FIG. 1, a catheter 20 constructed in accordance with principles of the present invention comprises a catheter body 22 having a proximal portion 24 and a distal portion 26. Proximal portion 24 can be coupled to distal portion 26 with a connection assembly 27 to allow pivoting or deflection of distal portion 26 relative to proximal portion 24. A proximal end of the catheter body 22 can have a handle 40 for manipulation by a user, a luer for connection to an aspiration or fluid delivery channel, or the like.

A debulking assembly, such as a cutter 28, abrasive member, or the like, is disposed within a lumen 30 of the catheter body 22. The cutter 28 is typically rotatable within the distal portion 26 about an axis that is parallel to the longitudinal axis of the distal portion 26 of catheter 20 and axially movable along the longitudinal axis. The cutter 28 can access target tissue through a side opening window 32 which is typically large enough to allow the cutter 28 to protrude through and move out of the window 32 a predetermined distance. The cutter is coupled to a cutter driver 34 through a coiled drive shaft 36. Actuation of a movable actuator or other input device 38 can activate the drive shaft 36 and cutter, move cutter 28 longitudinally over a cam so as to deflect the distal portion and move the cutter 28 out of cutting window 32. Camming of the cutter 28 can cause the distal portion 26 to pivot or deflect relative to the proximal portion 24 so as to deflect and urge the cutter into the tissue in the body lumen.

In some embodiments, the distal portion 26 of the catheter may be moved to an angled or offset configuration from the longitudinal axis of the proximal portion 24 of the catheter and the cutter 28. In some embodiments, the cutter 28 can also be deflected off of the axis of the proximal and/or distal portion of the catheter. Moving the distal portion 26 to an angled/offset position may cause a portion of the catheter to urge against a target tissue, may expose the cutter 28 through the window 32 or both, in various embodiments.

In catheters 20 of the present invention, proximal portion 24 is typically relatively flexible and distal portion 26 is typically relatively rigid. Additionally, many embodiments include a flexible distal tip 42. The flexible proximal portion 24 of the catheter is typically a torque shaft and the distal portion 26 is typically a rigid tubing. The torque shaft 24 facilitates transportation of the catheter body 22 and cutter 28 to the diseased site. The proximal end of the torque shaft 24 is coupled to a proximal handle 40 and the distal end of the torque shaft is attached to the distal, rigid portion 26 of the catheter through the connection assembly 27. The drive shaft 36 is movably positioned within the torque shaft 24 so as to rotate and axially move within the torque shaft 24. The drive shaft 36 and torque shaft 24 are sized to allow relative movement of each shaft without interfering with the movement of the other shaft. The catheter body will have the pushability and torqueability such that torquing and pushing of the proximal end will translate motion to the distal portion 26 of the catheter body 22.

Figure 1A:
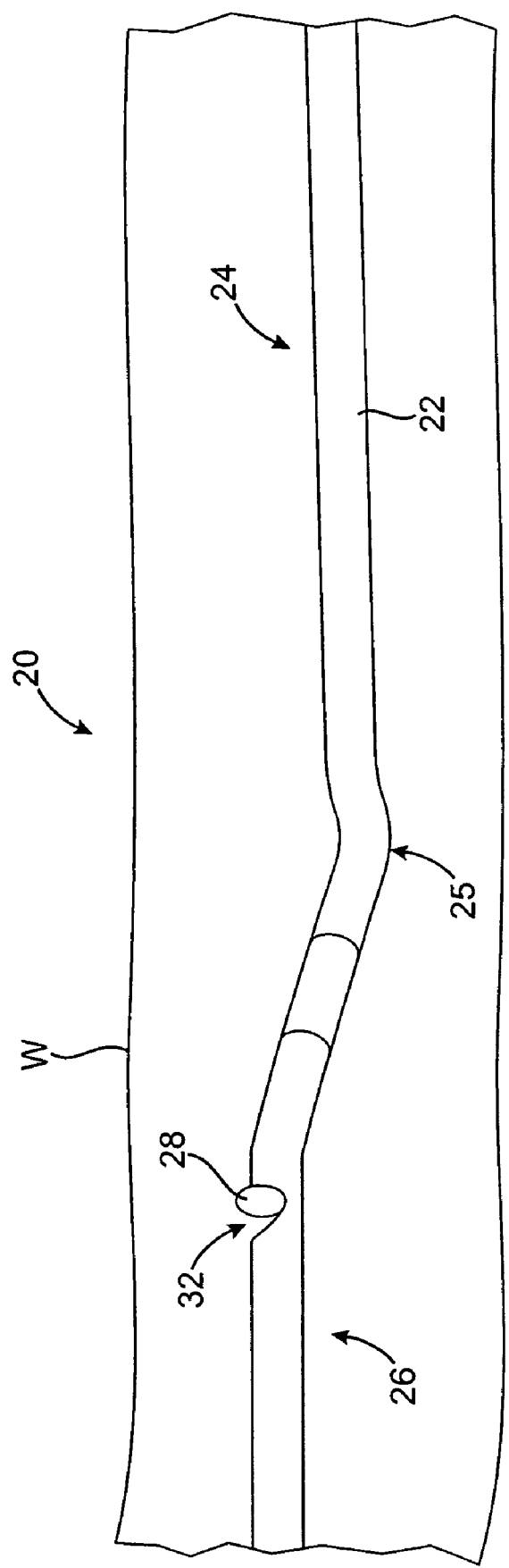
FIG. 1A is a side view of a portion of a debulking catheter as in FIG. 1, where the body has a rigid distal portion with a bend, according to one embodiment of the present invention.

Referring now to FIG. 1A, a catheter 20 as in FIG. 1 may have a flexible proximal portion 24 which additionally includes urging means 25. As shown in FIG. 1A, urging means 25 may comprise a rigid bent or curved shape towards the distal end of proximal portion 24, which may help urge the cutter 28 or other debulking apparatus toward a wall of a body lumen to enhance treatment. Such a rigid bend increases the working range of the catheter by allowing the cutter to be urged into a lumen wall across a wider diameter lumen.

In other embodiments, urging means 25 may take many other suitable forms. For example, a similar result to the rigid bend may be achieved by including a rigid distal portion that is not permanently bent but that is more rigid on one side than on the opposite side of catheter body 22. Thus, when proximal tension is applied to the proximal portion 24, as when proximal force is applied to the debulking apparatus to expose the cutter 28 through the window 32, the urging means 25 (i.e., the rigid distal portion of proximal portion 24) will cause the catheter body 22 to bend toward the less rigid side. The less rigid side will typically be the same side as the window 32, so that the window 32 and/or the cutter 28 will be urged against a wall of a body lumen by the bend. In still other embodiments, a shaped element may be introduced into catheter body to act as urging means 25. Any suitable urging means is contemplated.

Figure 2:
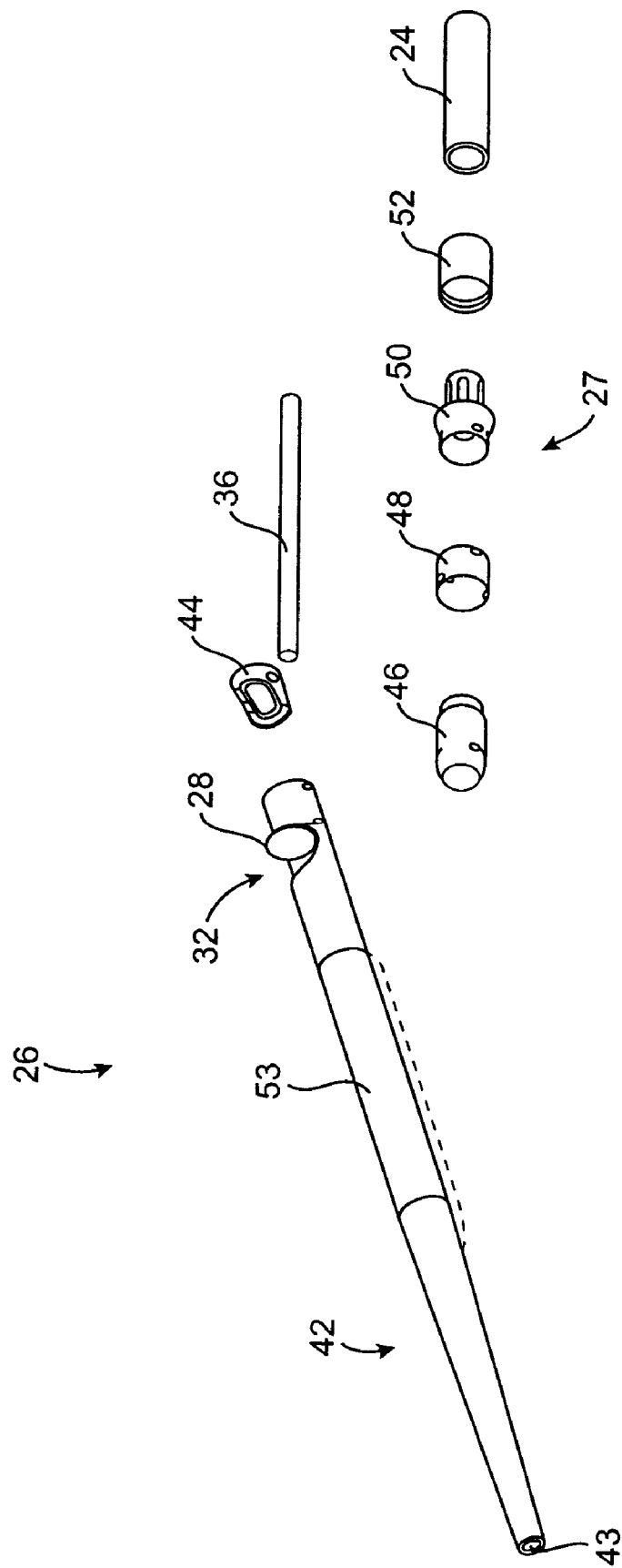
FIG. 2 is an exploded view of an exemplary distal portion of the debulking catheter of the present invention.

FIG. 2 illustrates an exploded view of a distal end of the catheter. In such embodiments, the catheter 10 includes a connection assembly 27, a rigid housing 26, a distal tip 42 that at least partially defines a collection chamber 53 for storing the severed atheromatous material, and a lumen that can receive the guidewire. The distal tip 42 can have a distal opening 43 that is sized to allow an imaging guidewire or conventional guidewire (not shown) to be advanced distally through the tip. In some embodiments, the distal tip 42 may also include a distal guidewire lumen (not shown) for allowing passage of a guidewire. For example, some embodiments may include a distal guidewire lumen having a length of between about 1.0 cm and about 5.0 cm, and preferably between about 2.0 cm and about 3.0 cm. Such a distal guidewire lumen may be used alone or in conjunction with a proximal guidewire lumen located on another, more proximal, portion of the catheter 20.

In embodiments including a distal guidewire lumen and a proximal guidewire lumen, the distal lumen may be configured to partially telescope within a portion of the proximal guidewire lumen, or vice versa. Such telescoping lumens may be used in embodiments where the distal portion 26 of catheter body 22 is movable relative to the proximal portion 24. A telescoping lumen may enhance performance of the catheter 20 by allowing a guidewire to be maintained largely within a lumen and to not be exposed within the body lumen being treated. Telescoping lumens may have any suitable diameters and configurations to allow for sliding or otherwise fitting of one lumen within another.

As mentioned above, various embodiments of the invention may allow for deflection of a portion of a catheter, exposure of a tissue debulking assembly through a window, or both. In some embodiments, movement of a tissue debulking assembly causes deflection of a portion of the catheter. In other embodiments, deflection of the catheter may cause a tissue debulking assembly to be exposed through a window on the catheter. In still other embodiments, there may be no causal relationship between deflection of the catheter and exposure of the debulking assembly—i.e., they may be separately caused.

As an example, a ramp or cam 44 may at least partially fit within the distal portion 26. As will be described in detail below, in some embodiments proximal movement of the cutter 28 over the ramp 44, causes the deflection of the distal housing 26 and guides cutter 28 out of cutting window 32. (In other embodiments, a ramp may be used to deflect the distal portion without extending the cutter out of the window.) Attached to the ramp 44 is a housing adaptor 46 that can connect one or more articulation member 48 to the distal tip to create an axis of rotation of the distal portion 26. The housing adaptor 46 and articulation member 48 allow the distal end of the catheter to pivot and bias against the body lumen. In the illustrated embodiment there are only one housing adaptor 46 and one articulation member 48, but it should be appreciated that the catheters of the present invention can include, two, three, or more joints (e.g., axis of rotation), if desired. Moreover, the axes of rotation can be parallel or non-parallel with each other.

The catheter can also include a shaft adaptor 50 and collar 52 to couple articulation member 48 to the torque shaft 22. Shaft adaptor 50 can connect the housing to the torque shaft and collar 52 can be placed over a proximal end of the shaft adaptor and crimped for a secure attachment. It should be appreciated by one of ordinary skill in the art that that while one exemplary catheter of the present invention has the above components that other catheters of the present invention may not include more or fewer of the components described above. For example, some components can be made integral with other components and some components may be left out entirely. Thus, instead of having a separate ramp 44, the ramp may be integrated with the distal tip to direct the cutter out of the cutting window.

Figures 3A, 3B:
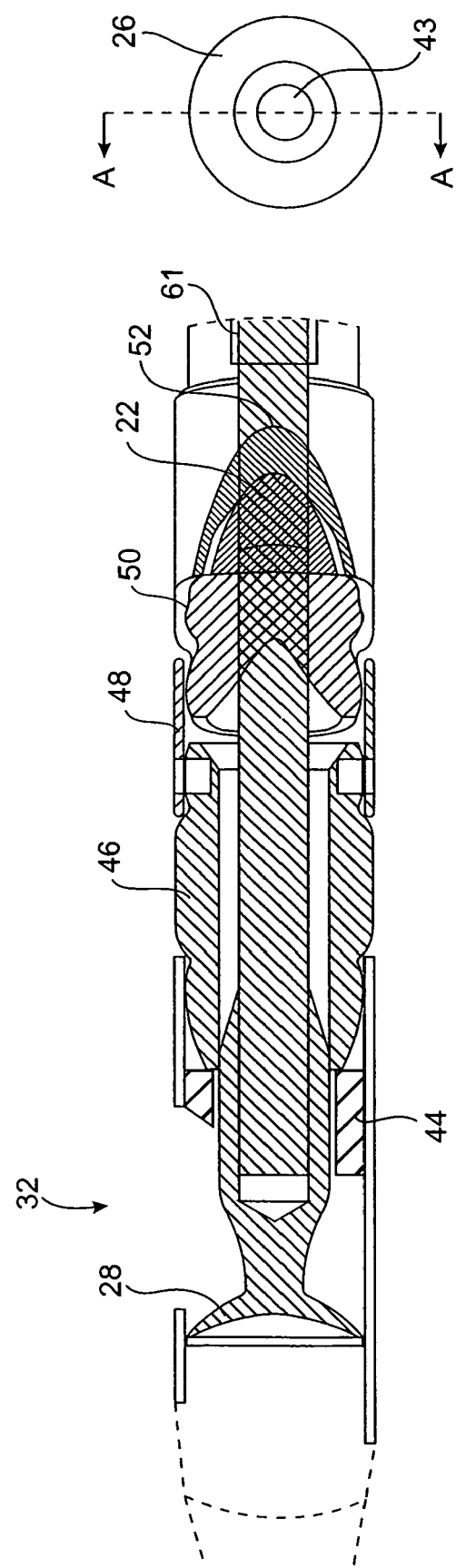
FIG. 3A is an end view of the distal portion of the debulking catheter of FIG. 1 in which the cutter is in a closed position in the catheter body.
FIG. 3B is a sectional view along Line A-A of FIG. 3A.
Figure 4A:
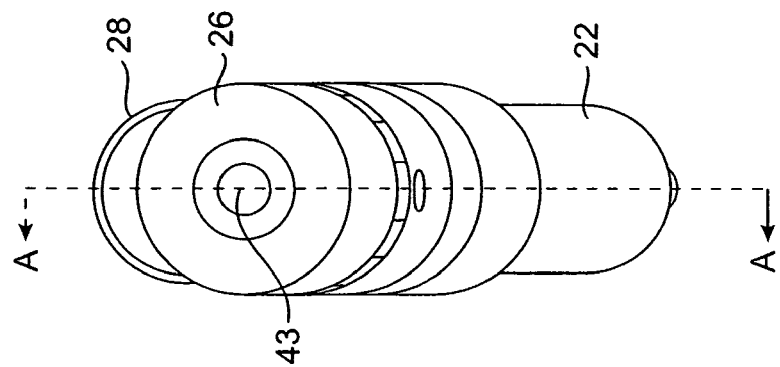
FIG. 4A is an end view of the distal portion of the debulking catheter of FIG. 1 in which the cutter is in an open position outside of the cutting window.
Figure 4B:
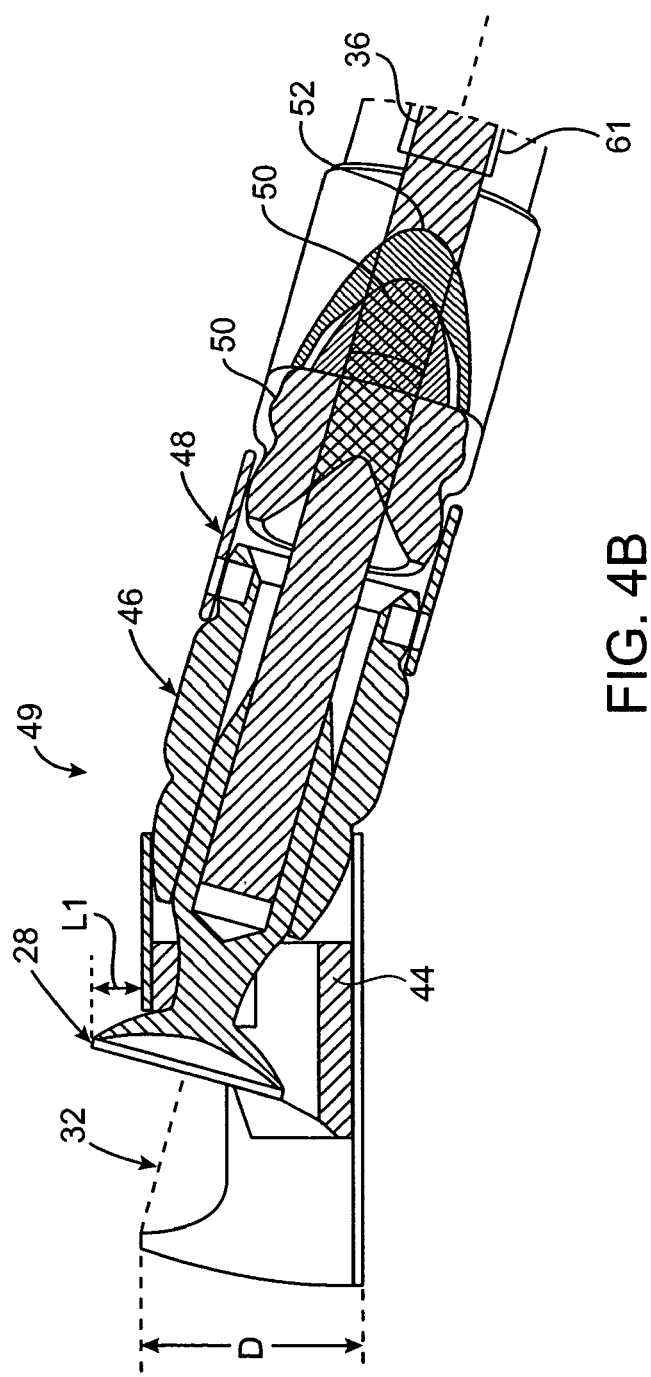
FIG. 4B is a sectional view along Line A-A of FIG. 4A.

As shown in FIGS. 3-5, the cutters 28 of the present invention will generally be movable between two or more positions. During advancement through the body lumen, the cutter will generally be in a neutral position (FIGS. 3A and 3B) in which the cutter 28 is distal of cutting window 32. In some embodiments, an imaging device (not shown) can be coupled to cutter 28 so as to image the body lumen through cutting window 32 when cutter 28 is in the neutral position. Once the catheter 20 has reached the target site, the cutter 28 can be moved to an open position (FIGS. 4A and 4B) in which the cutter 28 is moved to a proximal end of the cutting window 32 and will extend out of the cutting window 32 a distance L1 beyond an outer diameter D of the rigid portion 26. In most embodiments, in the open position, the cutter will have deflected the distal portion and the cutter's axis of rotation will generally be in line with connection assembly 27 but angled or offset from longitudinal axis of the distal portion of the catheter body.

Optionally, in some embodiments, cutter 28 can be moved to a packing position, in which the cutter is moved distally, past the neutral position, so as to pack the severed tissue into a distal collection chamber 53 (FIGS. 5A and 5B). It should be appreciated however, that while the exemplary embodiment moves the cutter to the above described positions, in other embodiments of the present invention the cutter can be positioned in other relative positions. For example, instead of having the neutral position distal of the cutting window, the neutral position may be proximal of the window, and the open position may be along the distal end of the cutting window, or the like.

Referring again to FIGS. 4A and 4B, the interaction of the components of the rigid distal portions 26 in one exemplary embodiment of the present invention will be further described. As shown in FIG. 4B, the cutting window 32 is typically a cutout opening in the distal portion 26. While the size of the cutting window 32 can vary, the cutting window should be long enough to collect tissue and circumferentially wide enough to allow the cutter to move out of the cutting window during cutting, but sized and shaped to not expel emboli into the vasculature. Cams or ramp 44 (shown most clearly in FIG. 4B) can be disposed in the distal portion of the catheter body to guide or otherwise pivot the cutter 28 out of the cutting window 32 as the cutter 28 is pulled proximally through tensioning of drive shaft 36.

A joint is located proximal to the cutting window 32 to provide a pivot point for camming of the distal portion 26 relative to the proximal portion 24. The bending at a flexible joint 49 is caused by the interaction of cams or ramps 44 with cutter 28 and the tensile force provided through drive shaft 36. In the exemplary configuration, the joint includes a housing adaptor 46 that is pivotally coupled to the distal rigid portion 26. As shown in FIGS. 4A and 4B, the resulting pivoting of the rigid distal portion 26 relative to the proximal portion causes a camming effect which urges the distal housing against the body lumen wall without the use of urging means (e.g., a balloon) that is positioned opposite of the cutting window. Thus, the overall cross sectional size of the catheter bodies can be reduced to allow the catheter to access lesions in smaller body lumens. In exemplary embodiments, the distal housing can deflect off of the axis of the proximal portion of the catheter typically between 0° degrees and 30° degrees, usually between 5° degrees and 20° degrees, and most preferably between 5° degrees and 10° degrees. The angle of deflection relates directly to the urge. Urge, however, does not necessarily relate to force but more to the overall profile of the catheter. For example, the greater the angle of deflection, the larger the profile and the bigger the lumen that can be treated. The ranges were chosen to allow treatment of vessels ranging from less than 2 mm to greater than 3 mm within the limits of mechanical design of the components. It should be appreciated however, that the angles of deflection will vary depending on the size of the body lumen being treated, the size of the catheter, and the like.

In some embodiments, the deflection of the distal portion 26 of the catheter urges the cutter into position such that distal advancement of the entire catheter body can move the rotating cutter through the occlusive material. Because the cutter is moved a distance L1 beyond the outer diameter of the distal portion of the catheter and outside of the cutting window, the user does not have to invaginate the tissue into the cutting window. In some embodiments, for example, the cutter can be moved between about 0.025 mm and about 1.016 mm, and preferably between about 0.025 mm and about 0.64 mm, beyond the outer dimension of the distal housing. It should be appreciated that the cutter excursion directly relates to the depth of cut. The higher the cutter moves out of the cutting window the deeper the cut. The ranges are chosen around efficacy without risk of perforation of the body lumen.

Some embodiments of the catheter include a shuttle mechanism or other similar mechanism for temporarily locking the catheter in a cutting position. FIGS. 3C and 3D illustrate such an embodiment in the neutral, non-cutting position. Such embodiments generally include a shuttle member 45 and a shuttle stop member 42. The shuttle stop member 42 is typically disposed at an angle, relative to a longitudinal axis through the catheter. FIGS. 4C and 4D show the same embodiment in the cutting position. When the cutter 28 is moved into the cutting position in such embodiments, the shuttle member 45 falls into the shuttle stop member 42 and thus locks the debulking apparatus in a cutting position. To unlock the debulking apparatus, the cutter 28 may be advanced forward, distally, to release the shuttle member 45 from the shuttle stop member 42.

Some embodiments including a shuttle mechanism will also include two joints in catheter body 22. Thus, catheter body 22 will include a proximal portion 26, a distal portion 24 and a middle portion. When shuttle mechanism is activated to expose cutter 28 through window 32, the middle portion may orient itself at an angle, relative to the proximal and distal portions, thus allowing cutter to be urged towards a side of a lumen. Such a two-jointed configuration may provide enhanced performance of the catheter 20 by providing enhanced contact of the cutter 28 with material to be debulked from a body lumen.

Pushing the entire catheter across a lesion removes all or a portion of the lesion from the body lumen. Severed tissue from the lesion is collected by directing it into a collection chamber 53 in the tip via the cutter 28. Once the catheter and cutter 28 have moved through the lesion, the cutter 28 can be advanced distally to a "part off position" in which the cutter is moved back into the cutting window 32 (FIG. 3B). The tissue is collected as the severed pieces of tissue are directed into a collection chamber 53 via the distal movement of cutter 28 and catheter. The collection chamber 53 of the tip and distal portion 26 acts as a receptacle for the severed material, to prevent the severed occlusive material from entering the body lumen and possibly causing downstream occlusions. The cutter 28 can interact with the distal edge of the cutting window to part off the tissue and thereafter pack the severed tissue into collection chamber 53 (FIG. 3B). In exemplary embodiments, the driver motor can be programmed to stop the rotation of the cutter at the part off position so that the cutter 28 can move to a third position (FIG. 5B) and pack the material in the collection chamber in the tip without rotation. Typically, the collection chamber 53 will be large enough to allow multiple cuts to be collected before the device has to be removed from the body lumen. When the collection chamber is full, or at the user's discretion, the device can be removed, emptied and reinserted over the guidewire via a monorail system, as will be described below.

In various embodiments, enhancements to the collection chamber 53 may be included. For example, in some embodiments the collection chamber 53 may be configured to be partially or completely translucent or radiolucent and a portion of the catheter surrounding or adjacent to the window 32 will be radiopaque. This combination of radiolucent collection chamber 53 and radiopaque material adjacent window 32 will enhance the ability of a user to determine how full the collection chamber 53 is, because the fullness of the collection chamber will be directly related to the distance the cutter 28 can advance forward into the collection chamber 53. By facilitating the assessment of collection chamber filling, these embodiments will reduce the need for manually withdrawing the catheter to examine the collection chamber 53.

In some embodiments, the collection chamber 53 may connect to the rigid housing by means of interlocking components, which interlock with complementary components on the rigid housing. Such components may resemble a screw-in configuration, for example. Interlocking components will provide a stable connection between the collection chamber 53 and the rigid housing while not increasing the outer diameter of either the chamber 53 or the housing. Generally, collection chamber 53 may be given any suitable configuration, shape or size. For example, collection chamber 53 in FIGS. 6-8 has a helical configuration. Alternatively, collection chamber 53 may include a series of circular members, straight linear members, one solid cylindrical or cone-shaped member or the like.

Figure 6:
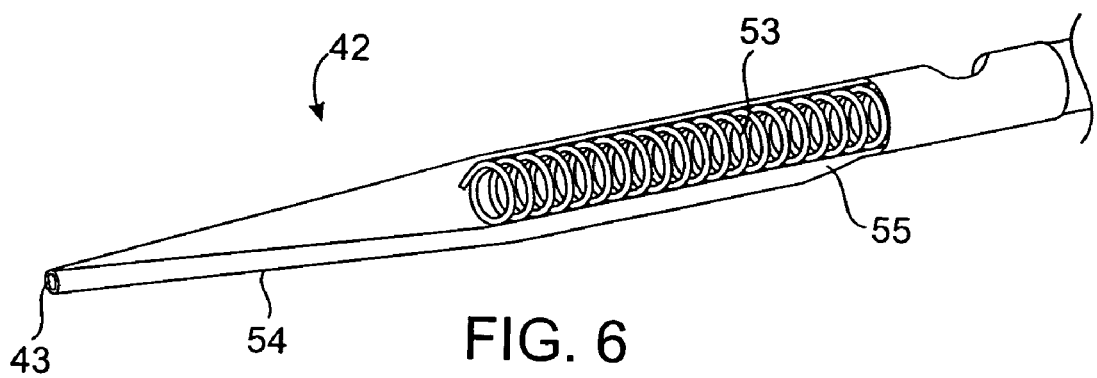
FIGS. 6 to 8 illustrate a monorail delivery system of the present invention.
Figure 7:
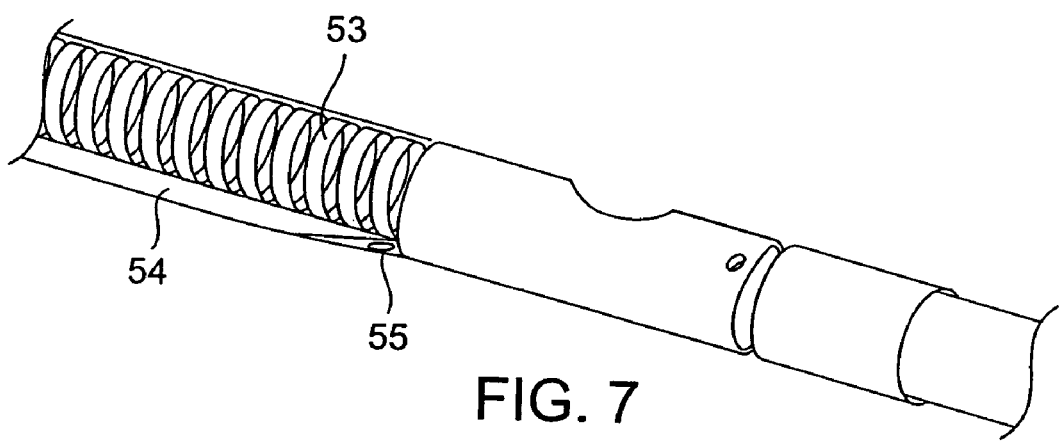
Figure 8:
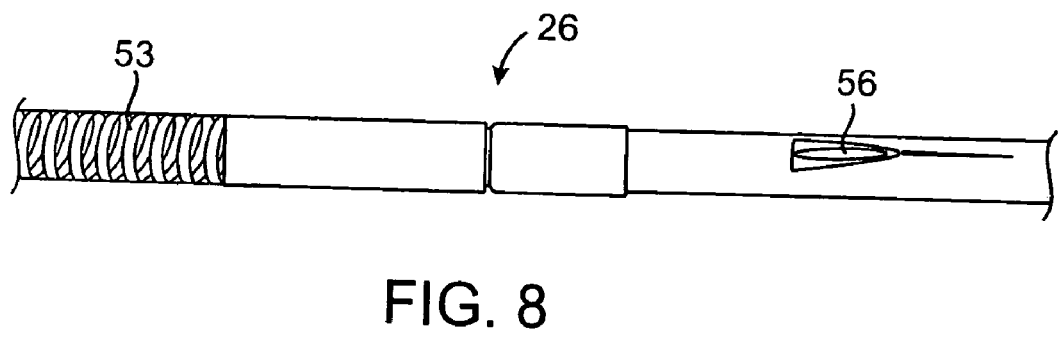

FIGS. 6 through 8 illustrate one exemplary monorail delivery system to assist in positioning the cutter 28 at the target site. For example, tip 42 of the catheter can include a lumen 54 having a distal opening 43 and a proximal opening 55 that is sized to receive a guidewire, having a diameter of about 0.014 in., about 0.018 in., about 0.032 in. or any other suitable diameter.

As shown in FIG. 8, the flexible proximal portion of the catheter body may also include a short lumen 56 (e.g., about 12 centimeters in length). In some embodiments, however, the guidewire lumen 56 may be disposed within or outside the flexible proximal portion of the catheter body and run a longer or shorter length, and in fact may run the entire length of the flexible portion 24 of the catheter body. In use, the guidewire can be disposed within lumen 56 on the flexible portion of the catheter body and exit the lumen at a point proximal to the rigid portion 26 of the catheter. The guidewire can then re-enter a proximal opening 55 in the tip lumen 54 and exit through distal opening 43 in the tip lumen. By moving the guidewire outside of the rigid portion 26 of the catheter body, the guidewire will be prevented from tangling with the cutter 28. Typically, tip lumen 54 will be disposed along a bottom surface of the tip and the lumen 56 will be disposed along a side of the proximal portion 22 of the catheter body so that the guidewire will be in a helical configuration. In various embodiments, the tip lumen 54 and the proximal lumen 56 can have any suitable combination of lengths. For example, in one embodiment the tip lumen 54 may have a length between about 1 cm and about 5 cm, more preferably between about 2 cm and about 3 cm, and the proximal lumen may have a length of between about 8 cm and about 20 cm, more preferably between about 10 cm and about 14 cm.

Figure 22A:
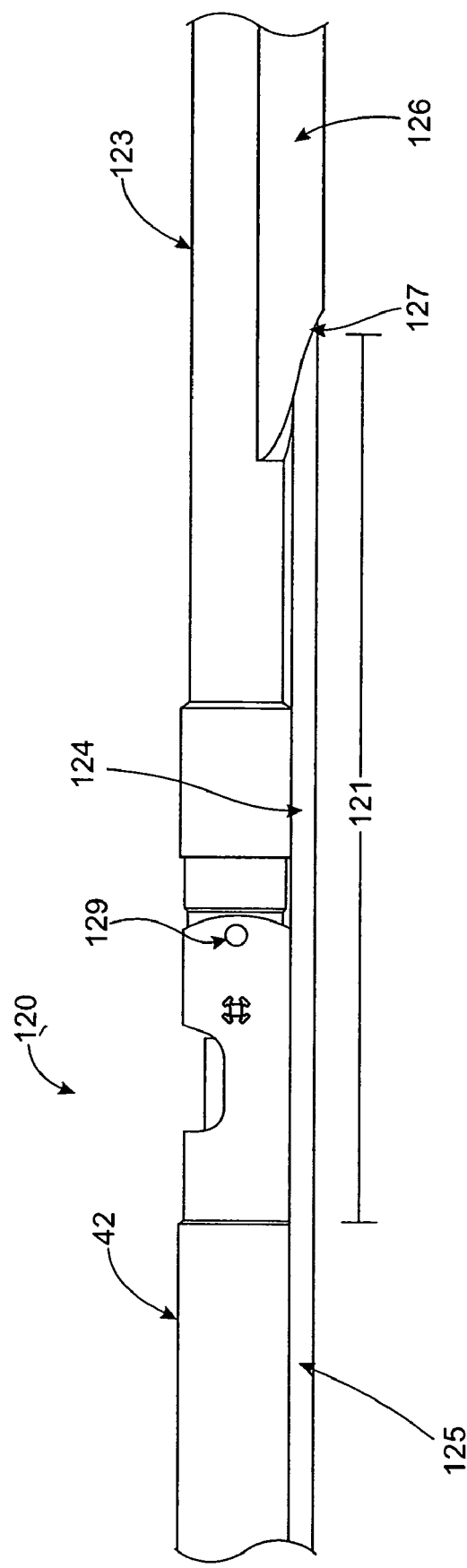
FIGS. 22A and 22B illustrate another embodiment of a guidewire lumen.
Figure 22B:
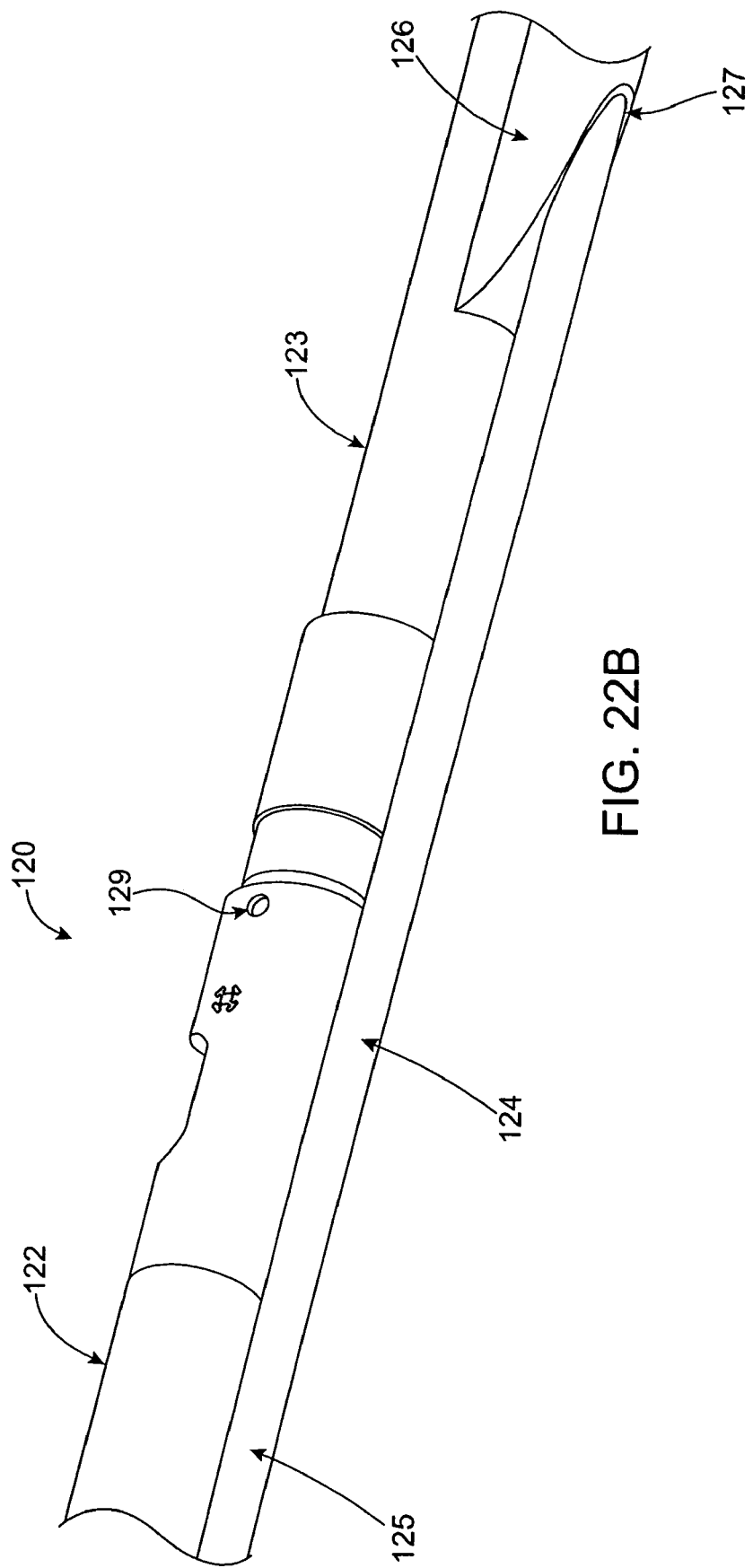

Referring now to FIGS. 22A and 22B, some catheters 120 of the present invention include a proximal guidewire lumen 126 coupled with the proximal portion of the catheter body 123, and a telescoping distal guidewire lumen 124 coupled with either the distal tip 122, part of the distal portion of the catheter body, or both. The telescoping lumen 124 will typically be attached to the tip 122 or a distal portion, but will also include an unattached portion 121, which will not be directly attached to any part of the catheter body. This unattached portion 121 (or "free floating lumen") protects a guidewire from contacting a body lumen in which the device is used and also allows the device to be moved more freely, without bending or kinking the guidewire. The telescoping guidewire 124 extends within the proximal lumen 126 at the distal opening 127 of proximal lumen 126. Again, the telescoping feature allows for movement of the catheter body while preventing or reducing bending of the guidewire. For example, in some embodiments catheter 120 allows for deflection of distal tip 122 and the distal portion of the catheter 120 relative to the proximal portion 123, for example by movement about a pivot point 129. Telescoping distal lumen 124 and proximal lumen 126 allow for this movement by allowing distal lumen 124 to telescope within proximal lumen 126. At the same time, distal lumen 124 protects a guide wire from exposure to a body lumen and/or bodily fluids.

Any suitable configurations and sizes of distal lumen 124 and proximal lumen 126 are contemplated. For example, in one embodiment distal lumen 124 may telescope within proximal lumen 126 by a distance of approximately 1 cm. Furthermore, a telescoping lumen 124 may be longer than distal lumens in other embodiments. For example, telescoping lumen 124 may have a length of between about 2 cm and about 10 cm, and preferably between about 5 cm and about 8 cm. As is apparent from the drawing figures, the outer diameter of telescoping distal lumen 124 is configured to fit within the inner diameter of proximal lumen 126. Generally, any combination of sizes, lengths, diameters and shapes of distal lumen 124 and proximal lumen 126 may be used, to allow telescoping of one into another.

The catheters of the present invention can include radiopaque markers so as to allow the user to track the position of the catheter under fluoroscopy. For example, as already described, a point or area around or adjacent to the window may be made radiopaque. In other embodiments, the rigid distal portion 26 can be radiopaque and radiopaque markers can be disposed on the flexible shaft. Typically, the markers 59 will be disposed along the top, proximal to the cutting window, and on the bottom of the catheter to let the user know the position of the cutter and cutting window relative to the target site. If desired, the top and bottom markers can be different shaped so as to inform the user of the relative orientation of the catheter in the body lumen. Because the guidewire will form a helix in its transition from lumen 56 to tip lumen 54, the user will be able to view the top and bottom radiopaque markers 59 without interference from the guidewire. Some embodiments of the catheter can also include a radiopaque cutter stop 61 (FIG. 3B) that is crimped to driveshaft 36 proximal of the cutter that moves with the cutter so as to let the user know when the cutter is in the open position.

FIGS. 9A through 11D show some exemplary embodiments of the cutter 28 of the present invention. The distal portion 60 of the rotatable cutter 28 can include a serrated knife edge 62 or a smooth knife edge 64 and a curved or scooped distal surface 66. The distal portion 60 may have any suitable diameter or height. In some embodiments, for example, the diameter across the distal portion 60 may be between about 0.1 cm and about 0.2 cm. A proximal portion 68 of the cutter 28 can include a channel 70 that can be coupled to the drive shaft 36 that rotates the cutter. As shown in FIGS. 10A-10C, some embodiments of the cutters can include a bulge or bump 69 that is provided to interact with a stent so as to reduce the interaction of the cutting edge with the stent. In any of the foregoing embodiments, it may be advantageous to construct a serrated knife edge 62, a smooth knife edge 64, or a scooped distal surface 66 out of tungsten carbide.

Figure 11C:
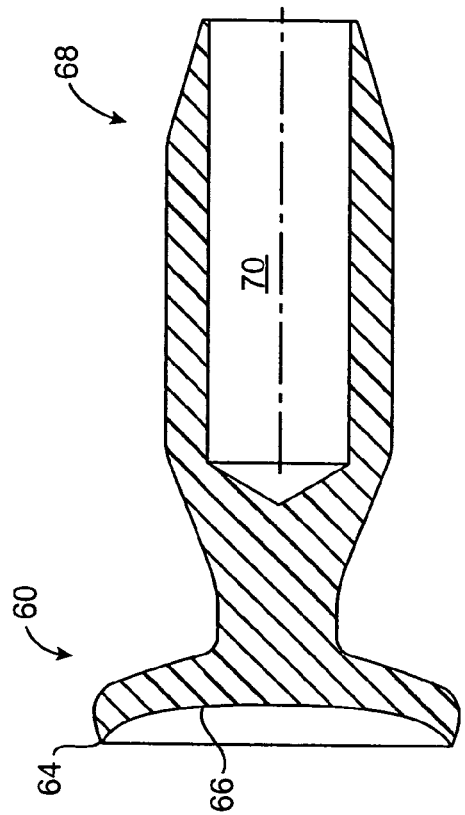
FIG. 11C is a sectional view of the cutter along Line C-C of the cutter of FIGS. 11A and 11B.
Figure 11A:
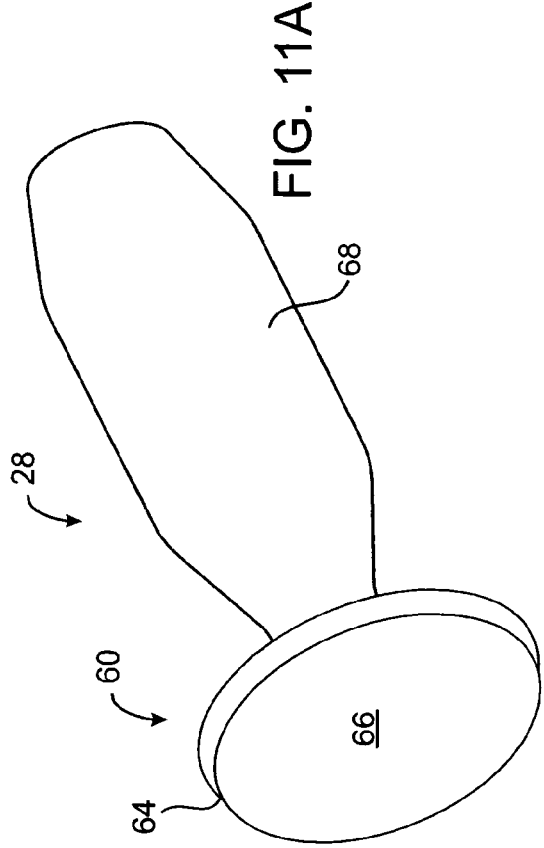
FIG. 11A is a perspective view of another in-stent restenosis cutter of the present invention.
Figure 11B:
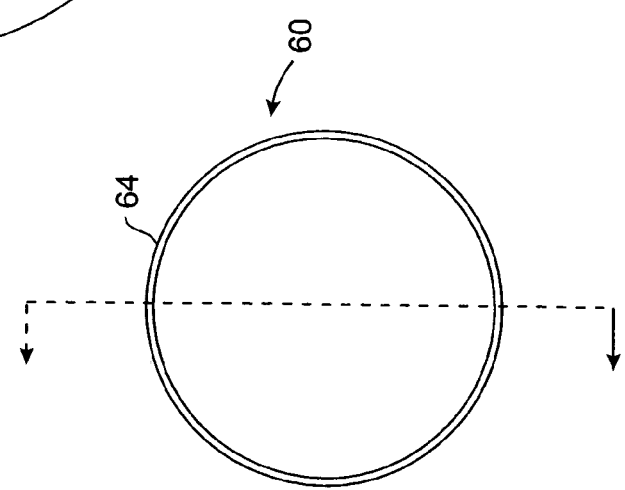
FIG. 11B is an end view of the cutter of FIG. 11A.
Figure 11D:
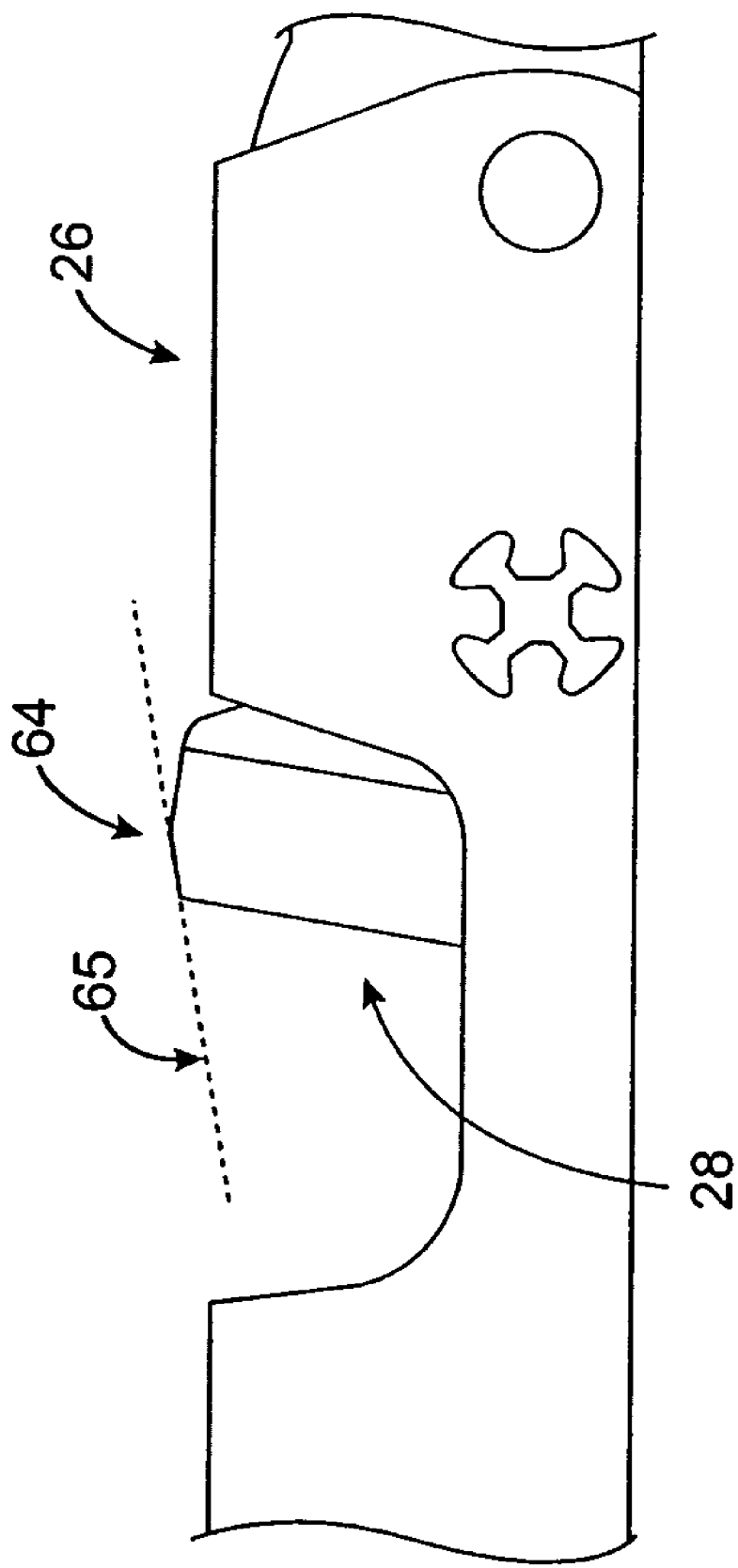
FIG. 11D is a side view of another embodiment of a cutter, shown partially within a catheter body.

Another embodiment of a cutter 28 suitable for use in the present invention is shown in side view within a catheter body distal portion 26 in FIG. 11D. In this embodiment, the cutter 28 has a beveled edge 64, made of tungsten carbide, stainless steel, titanium or any other suitable material. The beveled edge 64 is angled inward, toward the axis of rotation (or center) of the cutter 28, creating a "negative angle of attack" 65 for the cutter 28. Such a negative angle of attack may be advantageous in many settings, when one or more layers of material are desired to be debulked from a body lumen without damaging underlying layers of tissue. Occlusive material to be removed from a vessel typically has low compliance and the media of the vessel (ideally to be preserved) has higher compliance. A cutter 28 having a negative angle of attack may be employed to efficiently cut through material of low compliance, while not cutting through media of high compliance, by allowing the high-compliance to stretch over the beveled surface of cutter 28.

Figure 12:
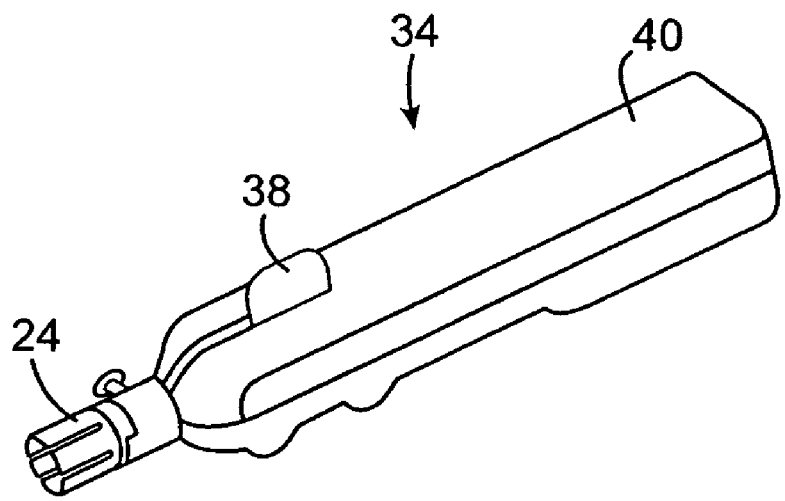
FIG. 12 illustrates a proximal handle and cutter driver of the present invention.
Figure 13:
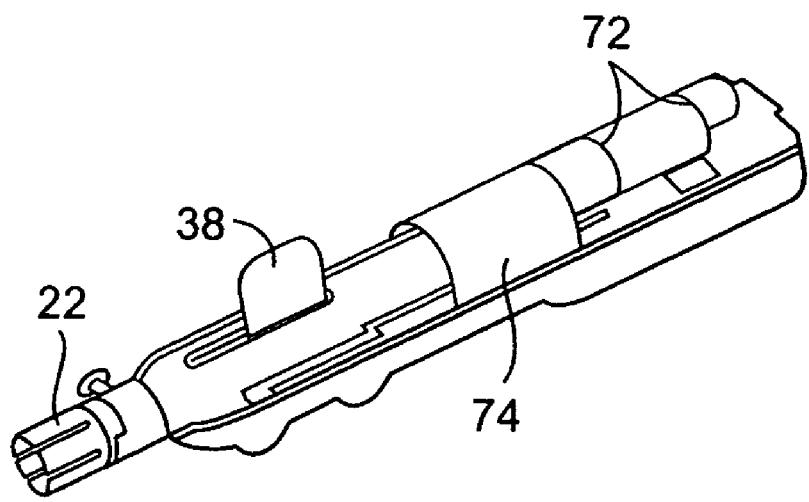
FIG. 13 illustrates a cutter driver with a handle cover removed.
Figure 14:
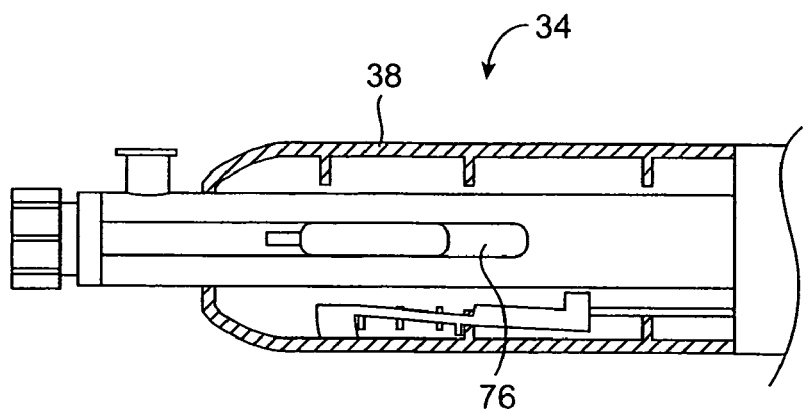
FIGS. 14 to 16 illustrate three positions of the lever for controlling the cutter.

FIGS. 12 through 16 illustrate an exemplary cutter driver 34 of the present invention. As shown in FIGS. 12 and 13, cutter driver 34 can act as the handle for the user to manipulate the catheters 20 of the present invention as well as a power source. Typically, the cutter drivers 34 of the present invention include a single input device, such as a lever 38 that controls the major operations of the catheter (e.g., axial movement to cause urging, rotation to cause cutting, and axial movement for packing). As shown in FIGS. 13 and 14, cutter driver 34 includes a power source 72 (e.g., batteries), a motor 74, a microswitch 76 for activating motor 74, and a connection assembly (not shown) for connecting the drive shaft 36 to the driver motor 74. In some embodiments, the drive motor can rotate drive shaft 36 between 1,000 rpm and 10,000 rpm or more, if desired.

Figure 15:
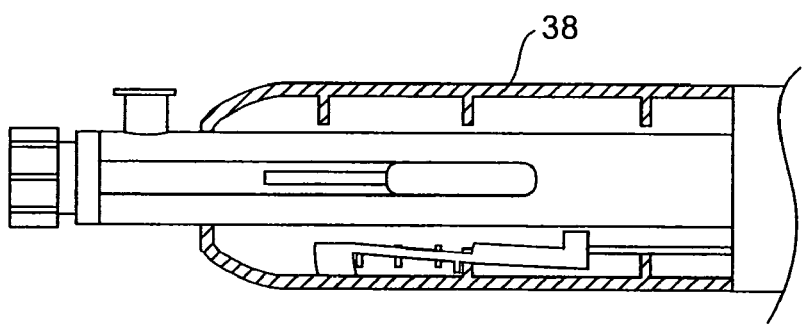
Figure 16:
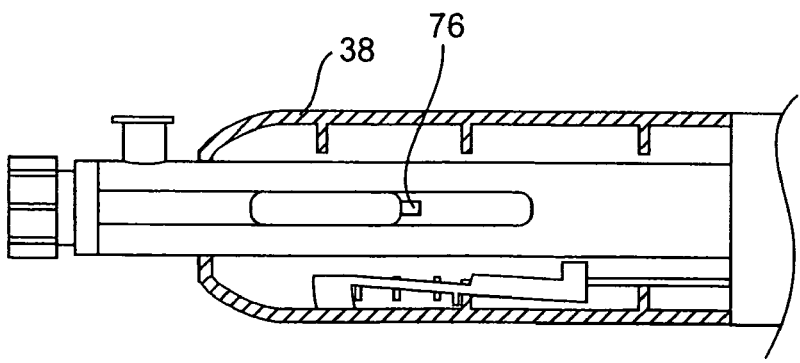

FIGS. 14 through 16 illustrate one exemplary method of operating cutter driver 34. In use, the catheter will be delivered to the target site with cutter driver unattached and the cutter in the neutral position (FIG. 3B). The cutter driver can be attached with the urge lever 38 in a neutral position (FIG. 14), which indicates that the cutter is closed, but not in a packing position. The user can then move the catheter (and cutter driver unit, if desired) to position the distal portion 26 of the catheter adjacent the target tissue. As shown in FIG. 15, to activate the rotation of the cutter, the urge lever 38 can be moved proximally from the neutral position to move the cutter proximally and out of cutting window 32 (FIG. 4B) and simultaneously depressing microswitch 76 to activate motor 74. At the end of the cutting procedure, as shown in FIG. 16, the user can push urge lever 38 completely forward to a distal position to push the cutter into a packing position (FIG. 5B). After the urge lever passes the middle of the travel, the microswitch 76 can be released so as to deactivate the cutter before reaching the packing position such that packing can occur without the cutter rotating. It should be appreciated, while the figures illustrate the use of an urge lever or thumb switch as an input device, the present invention can use other type of input devices, such as labeled buttons (e.g., close window, debulk tissue, and pack), or the like.

Advantageously, cutter driver 34 provides an automatic on/off control of the cutter 28 that is keyed to the position of the cutter. Such a configuration frees the user from the complicated task of remembering the sequence of operations to activate and deactivate the rotation and axial movement of the cutter.

While the cutter driver 34 is illustrated as a disposable battery powered unit, it should be appreciated that in other embodiments, the cutter driver can use other power sources to control the cutter driver. It should further be appreciated that other cutter drivers can be used with the present invention. While not preferred, it is possible to have separate controls to control the axial movement of the cutter and the rotation of the cutter.

Figure 17:
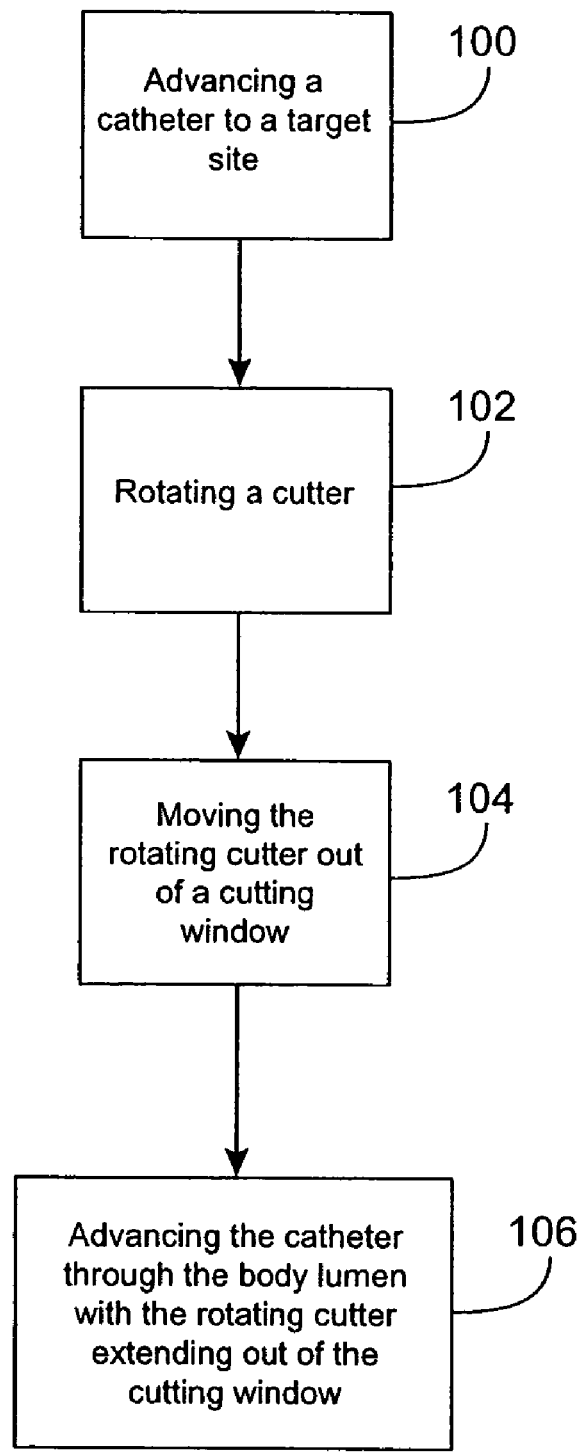
FIG. 17 is a simplified flow chart illustrating a method of the present invention.

Some exemplary methods of the present invention will now be described. One method of the present invention comprises delivering a catheter to a target site in the body lumen. A distal portion of the catheter can be deflected relative to a proximal portion of the catheter to expose a tissue debulking device in the catheter. The body lumen can be debulked with the exposed debulking device. Specifically, as shown schematically in FIG. 17, one specific method comprises advancing a catheter to a target site (Step 100). A cutter can be rotated and moved out of the cutting window (Steps 102, 104). Preferably, a distal portion of the catheter can be pivoted or deflected so as to position the cutter adjacent the target material. Thereafter, the catheter and the rotating cutter can be moved through the body lumen to remove the target material from the body lumen (Step 106).

Figure 18:
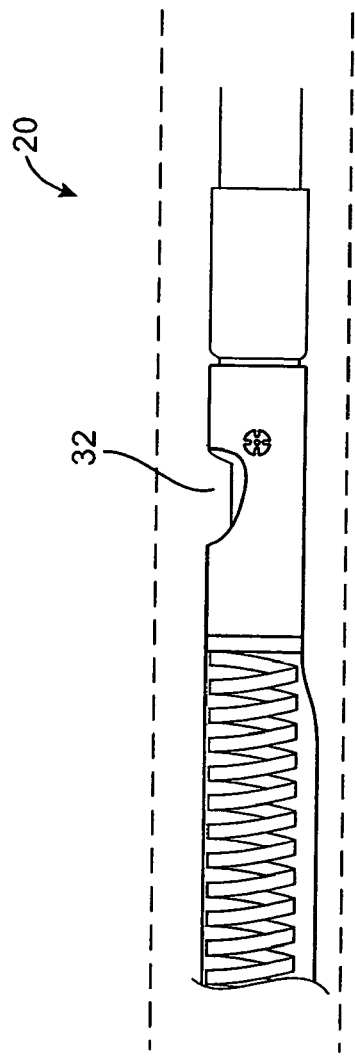
FIGS. 18 and 19 illustrate a method of the present invention.
Figure 19:
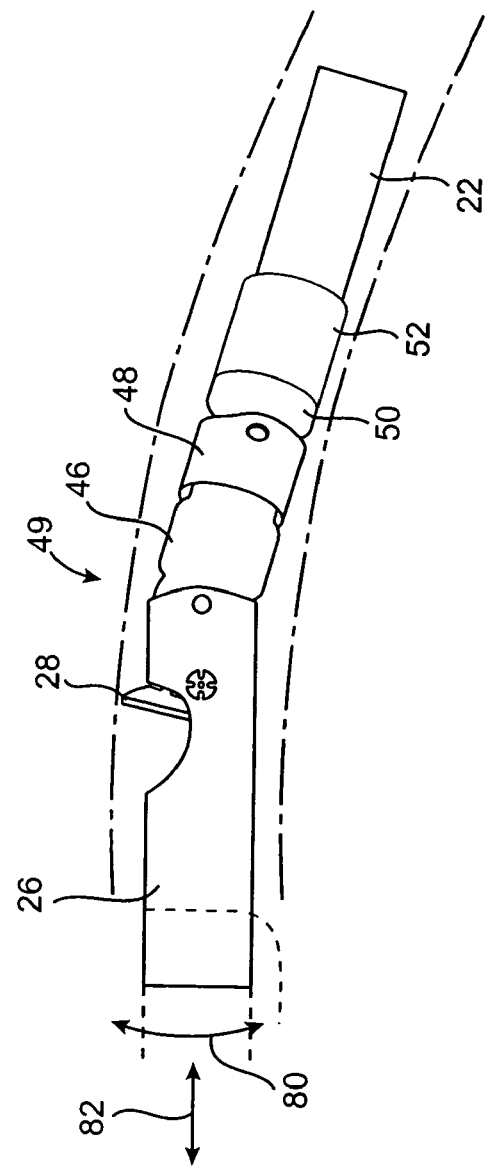

As shown in FIGS. 18 and 19, the catheter can be percutaneously advanced through a guide catheter or sheath and over a conventional or imaging guidewire using conventional interventional techniques. The debulking catheter 20 can be advanced over the guidewire and out of the guide catheter to the diseased area. As shown in FIG. 18, the window 32 will typically be closed (with the cutter or other debulking device 28 in a first, distal position). As shown in FIG. 19, catheter 20 will typically have at least one hinge or pivot connection to allow pivoting about one or more axes of rotation to enhance the delivery of the catheter into the tortuous anatomy without dislodging the guide catheter or other sheath. The cutter can be positioned proximal of the lesion. Optionally, a transducer, IVUS, or other imaging assembly can be used to verify the position of the debulking catheter.

Once the position of the catheter is confirmed, the cutter 28 will be retracted proximally and moved out of cutting window 32 to its second, exposed position. In some embodiments, movement of the cutter can deflect the distal portion of the catheter to increase the profile of the catheter at the target site. Movement of the cutter is typically caused by proximal movement of lever 38 and tensioning of drive shaft 36. Movement of the lever can be scaled to any desired ratio or a direct 1:1 ratio of movement between the handle and cutter. When the cutter is moved proximally it contacts ramp or cam surfaces so as to guide the cutter up and at least partially out of the cutting window 32. Additionally, as shown by arrow 80, the distal portion of catheter body 26 rotates about the joint 49 to provide an urging force for the cutter (and catheter body) to move toward the diseased area.

Thereafter, as shown by arrow 82 the operator can move the entire catheter body 22 through the lesion to dissect the tissue. As the cutter 28 and catheter body 22 are advanced distally through the lesion, tissue that is trapped between the cutting edge 52 and the cutting window 32 is severed from the body lumen. To part off the tissue, the operator can stop pushing the device distally and the cutter can be advanced distally inside the cutting window by advancing the handle 38. During the distal movement of the cutter, the cutter 28 rides back over the ramps 44 and directs the cutter back inside of the cutting window 32. Such movement causes the distal portion 26 of the catheter to move in line with the cutter and proximal portion 24 (FIG. 5B). When the cutter has moved to its distal position, the cutter parts off the severed tissue and urges the severed tissue inside of a collection chamber 53 in the distal tip 42. Optionally, after the cutter 28 has parted off the tissue, the lever 38 and thus the non-rotating cutter 38 can be advanced distally to pack the tissue into the collection chamber 53 (FIG. 5B). Use of the cutter to pack the severed tissue will allow the operator multiple specimens to be collected prior to removing the catheter 20 from the body lumen. When it is determined that the collection chamber is full, the catheter can be removed from the body lumen and the collection chamber can be emptied, and the excised tissue may be stored or tested as described above.

Figure 20:
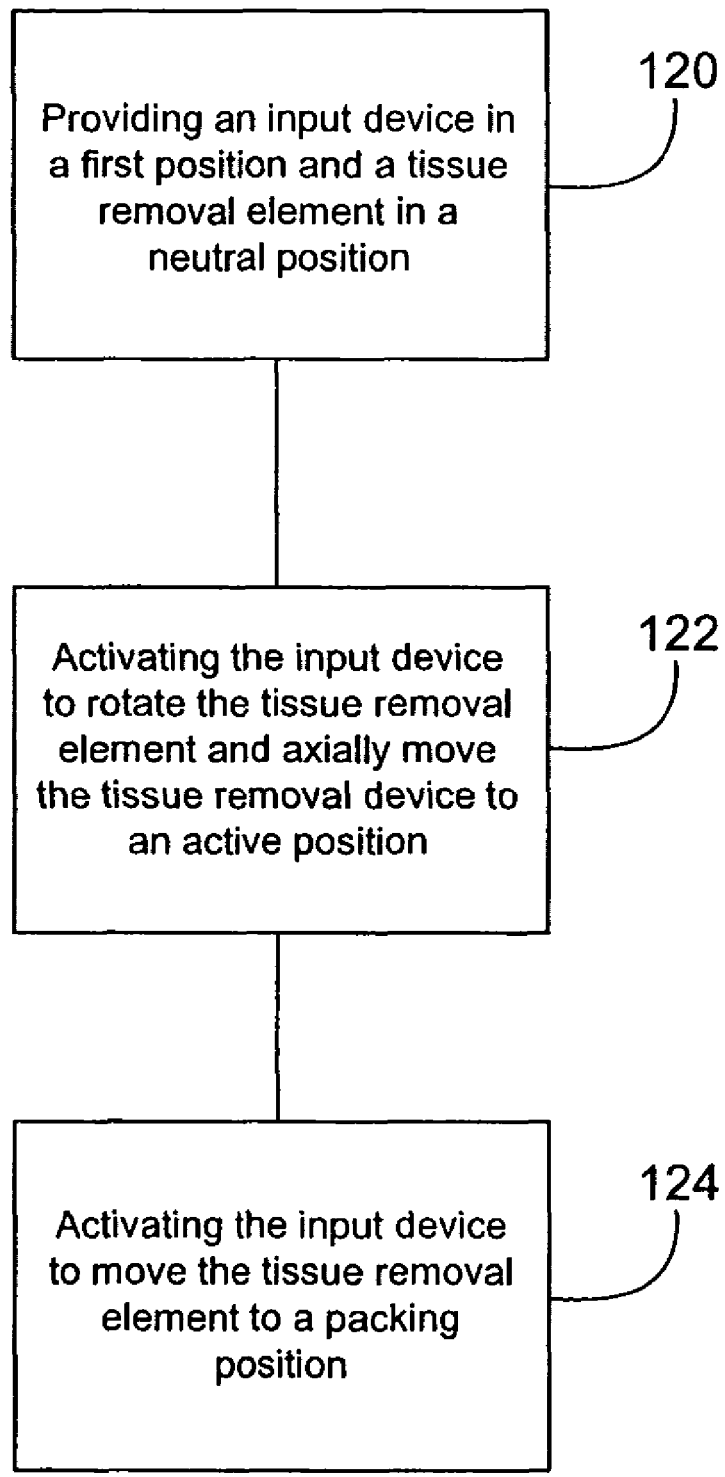
FIG. 20 schematically illustrates another method of the present invention.

In another method of the present invention, as shown in FIG. 20, an input device is disposed in a first position to position a tissue removal element in a neutral position (Step 120). The input device is activated to rotate the tissue removal element and to axially move the tissue removal device to an active position (Step 122). The input device can then be activated again to move the tissue removal element to a packing position (Step 124). In an exemplary embodiment, the input device is a lever or thumb switch that can be moved to correspond to the movement of a cutting element on the catheter. Thus, as the lever is moved proximally, the cutter is rotated and moved proximally to an open position. When the lever is moved to a distal position, the rotation of the cutter can be stopped and the cutter can be moved distally to pack severed tissue into a collection chamber.

Figure 21:
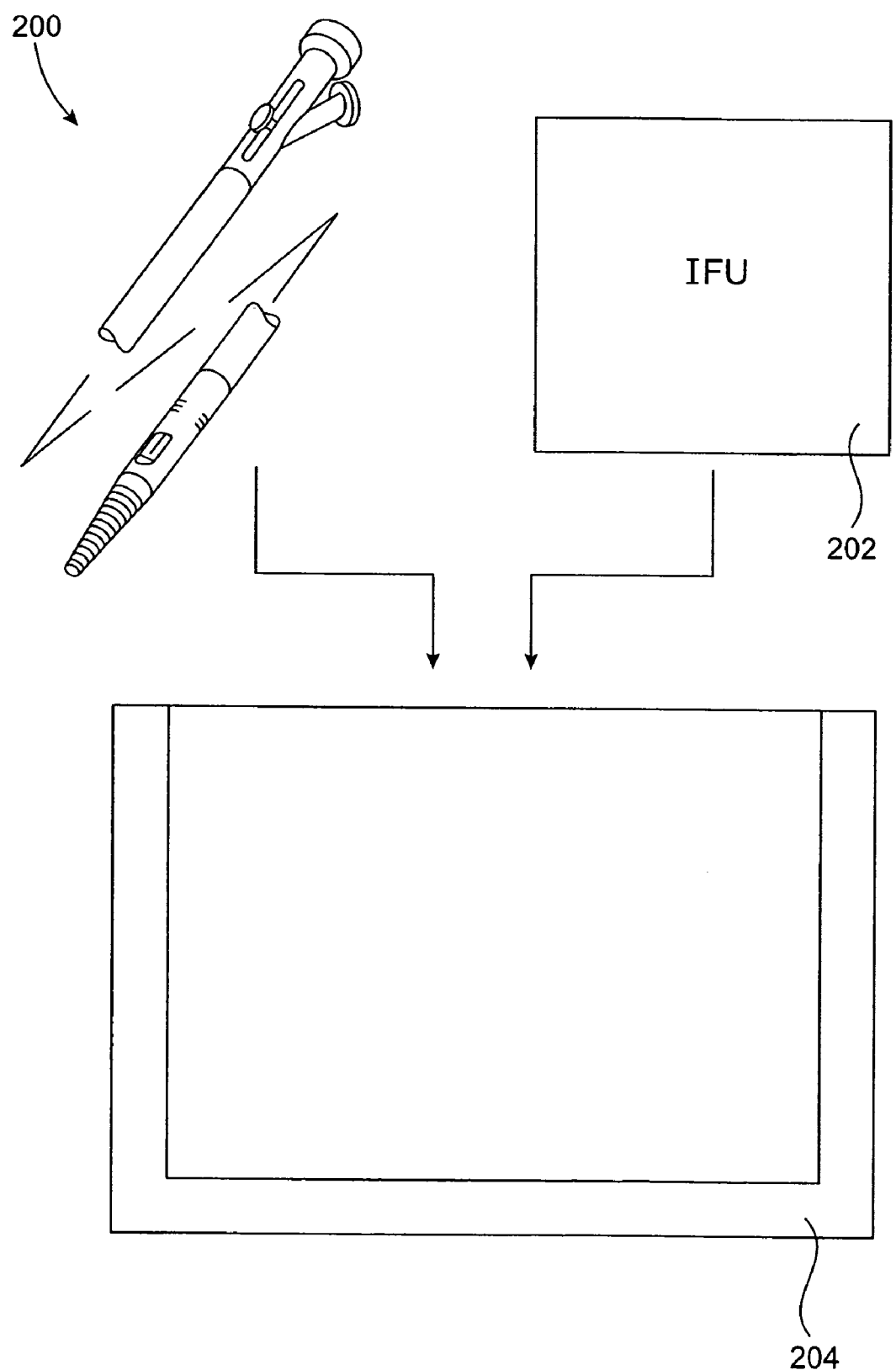
FIG. 21 illustrates a kit of the present invention.

Referring now to FIG. 21, the present invention will further comprise kits including catheters 200, instructions for use 202, and packages 204. Catheters 200 will generally be as described above, and the instruction for use (IFU) 202 will set forth any of the methods described above. Package 204 may be any conventional medical device packaging, including pouches, trays, boxes, tubes, or the like. The instructions for use 202 will usually be printed on a separate piece of paper, but may also be printed in whole or in part on a portion of the packaging 204.

While all the above is a complete description of the preferred embodiments of the inventions, various alternatives, modifications, and equivalents may be used. For example, while preferred cutters are moved proximally to move the cutter out of the cutting window, alternative embodiments may move the cutter distally to move the cutter out of the cutting window. Additionally, while most embodiments employ a cutter that extends out beyond the outer diameter of the cutting window, it may be possible to incorporate a cutter that stays within the diameter catheter body. Additionally, in some embodiments, the debulking assembly may be exposed through the window without causing a deflection of the distal portion of the catheter. Moreover, instead of having a distal tip that is rotatable relative to the proximal portion of the catheter, the catheter can include a shape memory material such that the catheter forms a jog or a pre-bent shape when it reaches its target area. Although the foregoing invention has been described in detail for purposes of clarity of understanding, it will be obvious that certain modifications may be practiced within the scope of the appended claims.

Example 1

Bilateral Appendage Comparison of Protein Content in Resected Arterial Plaque

For this study five patients with peripheral arteriolosclerosis were selected. Plaque tissue was removed from both legs in all patients. Some of the removed tissue was frozen. For analysis some of the frozen tissue was thawed and fixed with 10% formalin and subjected to routine paraffin processing. Five micron sections were cut, stained with elastic and Trichrome collagen stains and these slides were microscopically evaluated for general histology. Only the one patient (BAKCA) had some discordance between the stained protein content, the rest of the patients had the same lipid and protein levels as measured by immunohistochemistry in both their left and right legs. Gene array information was yielded from testing the material in the right and left legs of the patients.

Example 2

Tissue extraction and preparation is conducted as described in Example 1. The isolated tissue is analyzed for the following protein markers using standard techniques known in the art: interleukin-18, RANTES, fractalkine, interleukin-1-beta, matrix metalloproteinase-9, tumor necrosis factor-alpha, monocyte inflammatory protein alpha, E-selectin and P-selectin.

What is claimed is:

1. A composition, the composition comprising vascular tissue that has been excised in vivo from a subject, wherein the vascular tissue comprises at least one continuous strand of tissue that is removed from an interior wall of a vascular lumen in a living human body, wherein the continuous strand of tissue retains the in vivo structure of the tissue prior to its removal and is at least 2 cm in length along an axis of the vascular lumen.

2. The composition of claim 1 wherein the continuous strand of vascular tissue comprises 5 cm or greater in length.

3. The composition of claim 1 wherein the continuous strand of vascular tissue comprises 7 cm or greater in length.

4. The composition of claim 1 wherein the continuous strand of vascular tissue comprises 10 cm or greater in length.

5. The composition of claim 1 wherein the continuous strand of vascular tissue comprises 15 cm or greater in length.

6. The composition of claim 1 which comprises a plurality of continuous strands.

7. The composition of claim 6, wherein the plurality of strands are collected from a single vascular lumen.

8. The composition of claim 6, wherein the plurality of strands are collected from a single vascular atheroma or plaque.

9. The composition of claim 1 wherein the continuous strand has a mass per length of at least 0.45 mg/mm.

10. The composition of claim 1 wherein the continuous strand has a mass per length of at least 0.50 mg/mm.

11. The composition of claim 1 wherein the continuous strand has a mass per length of at least 0.60 mg/mm.

12. The composition of claim 1 wherein the continuous strand has a mass per length of at least 0.65 mg/mm.

13. The composition of claim 1 wherein the continuous strand has a mass per length of at least 0.70 mg/mm.

14. The composition of claim 1, wherein the vascular tissue comprises tissue excised from the coronary artery.

15. The composition of claim 1, wherein the composition is preserved in such a manner that the vascular tissue retains its in vivo structure.

16. A composition comprising vascular tissue that has been excised in vivo from a subject, wherein the vascular tissue comprises at least one continuous strand of tissue that is removed from an interior wall of a vascular lumen in a living human body, wherein the continuous strand of tissue retains the structure of the tissue prior to its removal, is at least 2 cm in length along an axis of the vascular lumen, and has a depth of at least 0.1 mm, wherein depth is a dimension which is radial to an axis of the lumen.

17. The composition of claim 16 wherein the continuous strand has a depth of at least 0.25 mm wherein depth is a dimension which is radial to the axis of the lumen.

18. The composition of claim 16 wherein the continuous strand has a depth of at least 0.33 mm wherein depth is a dimension which is radial to the axis of the lumen.

19. The composition of claim 16 wherein the continuous strand has a depth of at least 0.5 mm wherein depth is a dimension which is radial to the axis of the lumen.

20. The composition of claim 16 which comprises a plurality of continuous strands.

21. The composition of claim 20, wherein the plurality of strands are collected from a single vascular lumen.

22. The composition of claim 20, wherein the plurality of strands are collected from a single vascular atheroma or plaque.

23. The composition of claim 16 wherein the continuous strand has a mass per length of at least 0.45 mg/mm.

24. The composition of claim 16 wherein the continuous strand has a mass per length of at least 0.50 mg/mm.

25. The composition of claim 16 wherein the continuous strand has a mass per length of at least 0.60 mg/mm.

26. The composition of claim 16 wherein the continuous strand has a mass per length of at least 0.65 mg/mm.

27. The composition of claim 16 wherein the continuous strand has a mass per length of at least 0.70 mg/mm.

28. The composition of claim 16, wherein the vascular tissue comprises tissue excised from the coronary artery.

29. The composition of claim 16, wherein the composition is preserved in such a manner that the vascular tissue retains its in vivo structure.

30. A composition of excised vascular tissue comprising at least one continuous strand of tissue that is removed from a vascular lumen in a living human body, wherein the tissue is removed by
   providing a catheter;
   inserting the catheter into an unhealthy region of a vascular lumen of the living human body;
   advancing the catheter within the vascular lumen in such a manner so as to excise vascular tissue there from to produce excised vascular tissue; and
   preserving the excised vascular tissue;
   wherein the excised vascular tissue comprises a continuous strand of tissue that retains the in vivo structure of the tissue prior to its removal from the living human body, has a length of at least 2 cm along the axis of vascular lumen, and further comprises both plaque and diseased tissue.

31. The composition of claim 30 wherein the continuous strand has a mass per length of at least 0.50 mg/mm.

32. The composition of claim 30 wherein the continuous strand has a mass per length of at least 0.55 mg/mm.

33. The composition of claim 30 wherein the continuous strand has a mass per length of at least 0.60 mg/mm.

34. The composition of claim 30 wherein the continuous strand has a mass per length of at least 0.65 mg/mm.

35. The composition of claim 30 wherein the continuous strand has a mass per length of at least 0.70 mg/mm.

36. The composition of claim 30 which comprises a plurality of continuous strands.

37. The composition of claim 30 wherein the plurality of strands are collected from a single vascular lumen.

38. The composition of claim 30 wherein the plurality of strands are collected from a single vascular atheroma or plaque.

39. The composition of claim 30, wherein the vascular tissue comprises tissue excised from the coronary artery.

40. A composition, the composition comprising vascular tissue that has been excised in vivo from a subject, wherein the vascular tissue has a first depth and being debulked from an interior wall of a vascular lumen having a second depth, wherein the depth of the excised vascular tissue is less than the depth of the wall of the vascular lumen, and wherein the vascular tissue comprises at least one continuous strand of tissue having a length of at least 2 cm along the axis of the vascular lumen.

41. The composition of claim 40, wherein the excised vascular tissue reflects the structural integrity of an in vivo tissue of the vascular lumen.

42. The composition of claim 41, wherein the excised vascular tissue has a depth selected from the group consisting of at least 0.1 mm, at least 0.25 mm, at least 0.33 mm, and at least 0.5 mm.

43. The composition of claim 40, wherein the excised vascular tissue was debulked from an interior wall of a vascular lumen in a body by use of a catheter,
   wherein the catheter comprises a catheter body, wherein the catheter body comprises:
      (a) a proximal portion and a distal portion, wherein the distal portion is deflectable with respect to the proximal portion and the distal portion further comprises a window,
      (b) a tissue debulking assembly comprising a tissue cutter, wherein the tissue debulking assembly is configured for being exposed through the window when the distal portion is deflected with respect to the proximal portion, and
      (c) a collection chamber positioned relative to the window such that the window opens up into the collection chamber;
   and wherein the excised vascular tissue comprises at least one continuous strand of tissue which continuous strand of tissue is at least 2 cm in length along an axis of the vascular lumen.

44. The composition of claim 43, wherein the excised vascular tissue further comprises diseased tissue excised from an unhealthy region of the vascular lumen.

45. A library comprising a plurality of systematically archived samples, wherein the samples comprise vascular tissue that has been excised in vivo from a subject, each sample containing at least one continuous strand of tissue that is removed from a vascular lumen in a living human body, wherein the continuous strand retains the in vivo structure of the tissue prior to its removal and is at least 2 cm in length along an axis of the vascular lumen.

46. The library of claim 45 wherein the samples are preserved so as to maintain the continuous strand intact.

47. The library of claim 45 wherein the samples are maintained in liquid nitrogen.

48. The library of claim 45 wherein the samples are maintained in paraffin.

49. The library of claim 45 wherein clinical information regarding patients from whom the samples were excised is maintained with the library.

50. The library of claim 45, wherein the vascular tissue further comprises diseased tissue excised from an unhealthy region of the vascular lumen.

* * * * *